United States Patent [19]
Hara et al.

[11] Patent Number: 5,640,959
[45] Date of Patent: Jun. 24, 1997

[54] ULTRASONIC DIAGNOSTIC APPARATUS

[75] Inventors: Yasushi Hara; Kazuhiro Watanabe; Atsuo Iida, all of Kawasaki, Japan

[73] Assignee: Fujitsu Limited, Kawasaki, Japan

[21] Appl. No.: 354,165

[22] Filed: Dec. 8, 1994

[30] Foreign Application Priority Data

Feb. 22, 1994 [JP] Japan ................................ 6-024360

[51] Int. Cl.⁶ ........................................................ A61B 8/00
[52] U.S. Cl. ........................................................ 128/661.01
[58] Field of Search ...................... 128/660.06, 660.07, 128/660.08, 661.01

[56] References Cited

U.S. PATENT DOCUMENTS

| | | | |
|---|---|---|---|
| 4,154,113 | 5/1979 | Engeler | 128/661.01 |
| 4,204,435 | 5/1980 | Bridoux et al. | |
| 4,242,912 | 1/1981 | Burckhardt et al. | |
| 5,123,415 | 6/1992 | Daigle | 128/661.01 |
| 5,148,810 | 9/1992 | Maslak et al. | 128/661.01 |

FOREIGN PATENT DOCUMENTS

| | | |
|---|---|---|
| 3916396 A1 | 11/1990 | Germany . |
| 2-114019 | 12/1990 | Japan . |
| 4-12971 | 6/1992 | Japan . |

OTHER PUBLICATIONS

J. Acoust. Soc. Am. 87(3), pp. 1218–1226, Mar. 1990, "An Alternative Structure For Adaptive Broadband Beamforming With Imperfect Arrays", by Kuang-Chih Huang, et al.

Primary Examiner—George Manuel
Attorney, Agent, or Firm—Staas & Halsey

[57] ABSTRACT

There is provided an ultrasonic diagnostic apparatus in which a plurality of piezoelectric transducers are arranged in a predetermined direction so as to transmit and receive ultrasonic waves to obtain a tomographic image on the inside of the subject. The ultrasonic diagnostic apparatus adopts such a scheme that a sector scan is electronically performed, and is capable of preventing deterioration of an image by reducing an influence of reflection of the ultrasonic waves from the ribs, and forming a good image improved in resolution. An intersection of scan lines at at least receiving end is set up between rib-to-rib which are located at the position deeper than the body surface of the subject. An aperture for transmitting and receiving of ultrasonic waves along the scan line of the central part of the sector configuration is wider than that along the scan line of the edge portion of the sector configuration.

35 Claims, 18 Drawing Sheets

1

ULTRASONIC DIAGNOSTIC APPARATUS

BACKGROUND OF THE INVENTION

1. Field of the Invention

The present invention relates to an ultrasonic diagnostic apparatus in which a plurality of piezoelectric transducers are arranged in a predetermined direction so as to transmit and receive ultrasonic waves to obtain a tomographic image on the inside of the subject, and more particularly to an ultrasonic diagnostic apparatus adopting such a scheme that a sector scan is electronically performed.

2. Description of the Related Art

Hitherto, there has been used an ultrasonic diagnostic apparatus in which ultrasonic waves are transmitted toward the subject, specially a living body and ultrasonic waves reflecting from a tissue within the living body are received by piezoelectric transducers to generate received signals, and an image of the living body is displayed on the basis of the received signals, thereby facilitating a diagnostic of an intestinal disease or the like in the living body.

FIG. 23 is a schematic diagram showing a functional structure of an ultrasonic diagnostic apparatus. The ultrasonic diagnostic apparatus 100 is provided with, for example, 64 piezoelectric transducers (hereinafter, it may happen that these are each referred to as "element") 12_1, 12_2, ..., 12_64, which are arranged as a strip. Those elements 12_1, 12_2, ..., 12_64 are applied to a body surface of the subject (not illustrated), and then a transmitting circuit 102 sends out pulse signals to the piezoelectric transducers in their associated timings, respectively. The pulse signals are converted into high voltage pulses by the associated transmitting driver 103_1, 103_2, ..., 103_64, respectively. The converted high voltage pulses are applied to the elements 12_1, 12_2, ..., 12_64, respectively, so that ultrasound beams emanate from the elements 12_1, 12_2, ..., 12_64 toward the inside of the subject.

The ultrasonic waves reflecting from the inside of the subject again return to the elements 12_1, 12_2, ..., 12_64 and are received thereat. Signals, which are generated through receiving by the elements 12_1, 12_2, ..., 12_64, are amplified suitably by receiving amplifiers 104_1, 104_2, ..., 104_64, respectively, and then supplied to a beamformer circuit 105. The beamformer circuit 105 is arranged to delay the respective entered received signals and then to add the respective delayed received signals, so that the received signals can be generated along the ultrasound beams extending into the subject. The added received signals, which are outputted from the beamformer circuit 105, are applied to a signal transforming circuit 106 so as to be transformed into a displaying signal. The displaying signal outputted from the signal transforming circuit 106 is applied to a CRT display 107, so that a tomographic image 110 on the inside of the subject is displayed on a screen of the display 107.

Incidentally, when the piezoelectric transducers (elements) 12_1, 12_2, ..., 12_64 are generally named, they are denoted as the piezoelectric transducers (elements) 12, hereinafter. This is the similar as to the matter of the transmitting driver 103_1, 103_2, ..., 103_64, and the receiving amplifiers 104_1, 104_2, ..., 104_64.

FIG. 24 is a typical illustration of an example showing a relationship between an arrangement of the piezoelectric transducers and reflecting points of ultrasonic waves within the subject. In this figure, the axis of abscissas X denotes an arrangement direction of 64 pieces of piezoelectric element 12 applied to a body surface, and the axis of ordinates Z and the clinoaxis Z' denote the directions (each of them is referred to as a scan line) of traveling of ultrasound beams within the subject. Here, it is assumed that an acoustic velocity within the subject is uniform independently of a place.

In case of the formation of ultrasound beams having a focus at a point P1 within the subject, the transmitting circuit 102 (Cf. FIG. 23) sends out transmission pulse signals to the piezoelectric elements 12_1, 12_2, ..., 12_64 in their associated timings, respectively, such that the transmission pulse signals are delayed in accordance with a delay pattern corresponding to an arc R1 described with the point P1 in the center so that the ultrasonic waves emitted from the piezoelectric elements 12_1, 12_2, ..., 12_64 arrive simultaneously on the arc R1, in such a manner that taking account of an acoustic velocity within the subject, for example, the piezoelectric elements 12_31 and 12_32 at the center radiate the ultrasonic waves at the time point when the ultrasonic waves emitted from the piezoelectric elements 12_1 and 12_64 at the both ends arrive on the arc R1.

In a similar fashion to that of the formation of ultrasound beams having a focus at a point P1, ultrasound pulse beams having focuses at points P2 and P3, respectively, which travel toward a scan line Z direction, are formed by means of generating by the transmitting circuit 102 transmission pulse signals delayed in accordance with delay patterns corresponding to arcs R2 and R3, respectively.

Further, it is possible to form not only a scan line extending to a direction (Z direction) perpendicular to the arrangement direction X of the piezoelectric elements 12_1, 12_2, ..., 12_64 but also a scan line extending to a direction (Z' direction) oblique with respect to the arrangement direction X. Ultrasound pulse beams having focus at a point P4, which travel toward a scan line Z' direction, are formed through an adjustment of delay patterns for transmission pulse signals so that the ultrasonic waves emitted from the piezoelectric elements 12_1, 12_2, ..., 12_64 arrive simultaneously on an arc R4 described with the point P4 in the center.

This is the similar as to the matter of receiving. For example, the ultrasonic waves reflecting from the point P1 travels toward the piezoelectric elements 12_1, 12_2, ..., 12_64 with dispersion and arrive simultaneously on the arc R1. Here, the received signals involved in the ultrasonic waves reflecting from the point P1, which are derived from, for example, the piezoelectric elements 12_31 and 12_32 of the center, are delayed until the ultrasonic waves reflecting from the point P1 are received by the piezoelectric elements 12_1 and 12_64 of the both ends. In this manner, the respective received signals are delayed through a delay pattern corresponding to the arc R1 and the delayed received signals are added, thereby forming at the receiving end the equivalent ultrasound beams having a focus at a point P1 and extending to the scan line Z direction.

In a similar fashion to that of the formation of ultrasound beams having a focus at a point P1 at the receiving end, ultrasound beams having focuses at points P2 and P3, respectively, which extend to the scan line Z direction, are formed at the receiving end by means of delaying the respective received signals in accordance with delay patterns corresponding to arcs R2 and R3, respectively.

Further, ultrasound beams having focus at a point P4, which extend to the scan line Z' direction, are formed at the receiving end by means of delaying the respective received signals in accordance with a delay pattern corresponding to an arc R4.

Here, the ultrasonic waves transmitted from the piezoelectric elements 12_1, 12_2, ..., 12_64 toward the scan line Z direction first arrive at a shallow point P3 within the subject, then at a point P2 and finally at a point P1. Consequently, the ultrasonic waves reflecting from the point P3 reach the elements 12 earlier than the ultrasonic waves reflecting from the point P2. Likewise, the ultrasonic waves reflecting from the point P2 reach the elements 12 earlier than the ultrasonic waves reflecting from the point P1.

Hence, this aspect is utilized for a control of delay patterns in such a way that a delay pattern for the respective received signals derived through the piezoelectric elements 12_1, 12_2, ..., 12_64 is adjusted, in timing of receipt of the ultrasonic waves reflecting from the point P3, to provide a delay pattern corresponding to the arc R1; in timing of receipt of the ultrasonic waves reflecting from the point P2, to provide a delay pattern corresponding to the arc R2; and in timing of receipt of the ultrasonic waves reflecting from the point P1, to provide a delay pattern corresponding to the arc R3. In this manner, it is possible to implement a so-called receiving dynamic focus in which a focal point at the receiving end is sequentially shifted, as P1→P2→P3, extending to the scan line Z direction.

FIG. 25 is an illustration showing a pattern of weighting (amplification factor of each of the receiving amplifiers 104_1, 104_2, ..., 104_64) for the respective received signals derived through the elements 12_1, 12_2, ..., 12_64.

It is assumed that the center of a group of the elements (receiving aperture) for use in receiving is given by X=0. As a function representative of a pattern of weighting, generally, Gaussian function, which is expressed by formula (1), is adopted.

$$g(x)=exp\{-\alpha^2(X/XO)^2\} \quad (1)$$

where

α: weighting factor, and

XO: coordinates of end of receiving aperture.

The weighting factor α serves to determine a ratio of gain of the received signal derived through an element located away from the center (X=0) of the aperture.

It is known that the above-mentioned weighting of the received signals may reduce a side-lobe-level of the received ultrasound beams, thereby enhancing resolution.

Incidentally, while Gaussian function is shown in formula (1) as the weighting function, it is noted that the weighting function is not always Gaussian function. It is known that the use of, for example, a trapezium-like shaped weighting function, which approximates to Gaussian function, may also bring the substantially same result.

FIG. 26 is an illustration showing an example in which a size D (the number of elements used for receiving) of the receiving aperture is varied in a state that weighting is fixed.

It is also known that a receiving is performed, as shown in FIG. 26, temporarily using a part of the arranged elements for the purpose of, for example, a control of the intensity and resolution of the received signals at a shallow point and a deep point within the subject, but not using all of the arranged 64 pieces of elements.

This is similar to the matter of a transmission. It is known that a transmission is performed, temporarily using a part of the arranged elements for the purpose of, for example, a control of the intensity of the ultrasonic waves at a shallow point and a deep point within the subject, and a beam width of the transmitting ultrasound beam. There is also known such a technique of weighting that in transmission, in a similar fashion to that of the weighting shown in FIG. 26, the number of pulses of the transmission pulse signal, a pulse voltage and the like are controlled to transmit the ultrasonic waves, which are mutually different in an intensity, from the respective elements in the transmission aperture (a group of elements for use in transmission).

Next, taking account of the various techniques as to the ultrasonic diagnostic system as mentioned above, there will be described the conventional electronic sector scan type of ultrasonic diagnostic apparatus, which is used, for example, for observation of the heart, and the problems involved in such an apparatus.

The sector scan implies such a scanning scheme that as explained referring to FIG. 24, a scan line extending to a direction oblique with respect to the arrangement direction of the elements is formed and sequentially varied in the direction of the scan line so as to spread in a sector configuration in its entirety. The use of such a sector scan serves to form a sector shaped tomographic image 110 as illustrated in the screen of the CRT display 107 in FIG. 23.

FIG. 27 is a typical illustration showing the state of transmitting and receiving of the ultrasonic waves through adjacent ribs toward the heart using the conventional electronic sector scheme of ultrasonic diagnostic apparatus.

According to the conventional typical electronic sector scan type of ultrasonic diagnostic apparatus, a sector shaped tomographic image is formed in such a manner that as seen from FIG. 27, an amount of delay of each of the elements 12 applied to a body surface 11 at the time of transmitting and receiving is controlled so that the ultrasound beams are deflected right and left with the center 1 of the elements 12 in the center. In this manner, in order to form the tomographic image of the heart, a scan is performed, placing a group of elements between rib 10-to-rib 10 each being of 10 mm in an adult. Consequently, as to the aperture with respect to the scan direction (an arrangement direction of the elements, or the right and left direction in FIG. 27), there are two conflicting requirements, one of which is involved in a requirement in which the aperture is formed in size as smaller as possible in view of the fact that the scan is performed through adjacent ribs, another concerns a requirement in which the aperture is formed in size as large as possible to obtain a penetration. As common grounds, usually, the aperture with respect to the scan direction is set up with a size of the order of 10 mm–20 mm. Hence, the scan lines (areas 20) of the edge portions of the sector configuration, where the ultrasonic waves are larger in the deflection angle, involves such problems that the ultrasonic waves are obstructed by the ribs 10 and as a result an observer cannot see portions deeper than the ribs 10, and further multiple reflection echoes due to reflection from the ribs appear and as a result overall image is deteriorated.

FIG. 28 is a typical illustration showing a technique of removing or reducing a bad influence of the ribs, which technique is proposed in, for example, Japanese Utility Model Laid Open Gazette No. 114019/1990.

According to the proposal as noted above, arranging the piezoelectric transducers 12 as a concave sets up the center of curvature (an intersection of scan line-to-line) 2 of the transmitting and receiving wave surface within the human body, and a so-called linear scan is carried out through a ultrasonic propagation medium 14 within a water sack 15, thereby implementing the sector scan in which the center of curvature 2 is placed in the center independent of the ribs 10. However, according to this scheme, the ultrasonic waves are reflected on a boundary between a body surface 11 and the ultrasonic propagation medium 14 and as a result multiple reflection echoes emanate, and thus it is difficult to obtain a good image.

Japanese Patent Publication No. 12971/1992 proposes a method of improving the problem as to the above-mentioned multiple reflection.

FIGS. 29 and 30 are each a typical illustration useful for understanding the proposal disclosed in Japanese Patent Publication No. 12971/1992.

According to the system of this proposal, the scan is performed in such a manner that the ultrasound beams pass through substantially a fixed point (center 2) within the human body, using fixed or semi-fixed delay elements 17 each provided for the associated element, so as to obtain the equivalence to such a situation that as in the related art shown in FIG. 28, the elements 12 are arranged on the arc of a radius R from the center 2 of the sector scan within the human body. In this case, the focal position of the ultrasound beams is equal to the position of the center 2 within the human body. On the other hand, it is necessary for observation of the heart to provide a focus position of the order of 80–100 mm, and thus variable delay elements 19 for use in alteration of the focal position are used in combination. With respect to the aperture width, as shown in FIG. 30, there is provided the same effective aperture (L1'=L1·COS (θ)=L0) on each scan line. The number of elements forming an aperture on each scan line is about 7–9 pieces.

However, this system is poor in the number of transmitting and receiving elements and thus poor in resolution and penetration. In case of the general electronic sector type, the aperture is of about 20 mm, and is comprised of 60 pieces of element. According to such general electronic sector type, 50 pieces of element are used for transmission, and about 30 overall elements are used for receiving. Consequently, according to the conventional systems as proposed in FIGS. 29 and 30, the aperture area (the number of transmitting and receiving elements) is too little to form the converged ultrasound beam, and thus it is apparent that resolution is reduced and penetration is not attained.

SUMMARY OF THE INVENTION

In view of the foregoing, it is therefore an object of the present invention to provide an ultrasonic diagnostic apparatus capable of solving the above-mentioned problems, preventing deterioration of an image by reducing an influence of reflection of the ultrasonic waves from the ribs, and forming a good image improved in resolution.

To achieve the above-mentioned objects, according to the present invention, there is provided an ultrasonic diagnostic apparatus, as the first type of system, comprising:

transmitting and receiving means, having a plurality of piezoelectric transducers are arranged in a predetermined arrangement direction, for sequentially transmitting ultrasound beams along a plurality of scan lines from the piezoelectric transducers into a subject and for sequentially receiving ultrasonic waves along a plurality of scan lines with the piezoelectric transducers; and display means for displaying a tomographic image of the subject on the basis of received signals generated from said transmitting and receiving means, wherein said transmitting and receiving means are arranged to transmit and receive ultrasonic waves along a plurality of scan lines which are sequentially deflected as a sector in the arrangement direction and pass through a first predetermined point within the subject apart from said piezoelectric transducers, and performs transmitting and/or receiving of ultrasonic waves using a larger number of said piezoelectric transducers for transmitting and receiving of ultrasonic waves along the scan lines nearer a central part of the sector configuration.

It is preferable, in the first type of ultrasonic diagnostic apparatus as recited above, that a distance $d_1$ between said piezoelectric transducers and said first predetermined point is expressed by 1 mm$\leq d_1 \leq$6 mm.

Further, it is preferable that said transmitting and receiving means includes a scan line intersection shift means for shifting said first predetermined point to said arrangement direction and a depth direction within the subject.

To achieve the above-mentioned objects, according to the present invention, there is provided an ultrasonic diagnostic apparatus, as the second type of system, comprising:

transmitting and receiving means, having a plurality of piezoelectric transducers are arranged in a predetermined arrangement direction, for sequentially transmitting ultrasound beams along a plurality of scan lines from the piezoelectric transducers into a subject and for sequentially receiving ultrasonic waves along a plurality of scan lines with the piezoelectric transducers; and display means for displaying a tomographic image of the subject on the basis of received signals generated from said transmitting and receiving means, wherein said transmitting and receiving means are arranged to transmit ultrasonic waves along a plurality of scan lines which are sequentially deflected as a sector in the arrangement direction and pass through a second predetermined point within the subject apart from said piezoelectric transducers, and receive ultrasonic waves along a plurality of scan lines which are sequentially deflected as a sector in the arrangement direction and pass through a third predetermined point within the subject, the third predetermined point being set up to a place deeper than the second predetermined point.

It is preferable, in the second type of ultrasonic diagnostic apparatus as recited above, that a distance $d_2$ between said piezoelectric transducers and said second predetermined point is expressed by 1 mm$\leq d_2 \leq$3 mm, and a distance $d_3$ between said piezoelectric transducers and said third predetermined point is expressed by $d_2 < d_3 \leq$6 mm.

Further, it is preferable that said transmitting and receiving means includes scan line intersection shift means for shifting said second predetermined point and said third predetermined point to said arrangement direction and a depth direction within the subject.

To achieve the above-mentioned objects, according to the present invention, there is provided an ultrasonic diagnostic apparatus, as the third type of system, comprising:

transmitting and receiving means, having a plurality of piezoelectric transducers are arranged in a predetermined arrangement direction, for sequentially transmitting ultrasound beams along a plurality of scan lines from the piezoelectric transducers into a subject and for sequentially receiving ultrasonic waves along a plurality of scan lines with the piezoelectric transducers; and display means for displaying a tomographic image of the subject on the basis of received signals generated from said transmitting and receiving means, wherein said transmitting and receiving means are arranged to transmit ultrasonic waves along a plurality of scan lines which are sequentially deflected as a sector in the arrangement direction and pass through a fourth predetermined point on said piezoelectric transducers, and receive ultrasonic waves along a plurality of scan lines which are sequentially deflected as a sector in the arrangement direction and pass through a fifth predetermined point within the subject apart from said piezoelectric transducers.

It is preferable, in the third type of ultrasonic diagnostic apparatus as recited above, that a distance $d_5$ between said piezoelectric transducers and said fifth predetermined point is expressed by 1 mm$\leq d_5 \leq$6 mm. Further, it is preferable, in the third type of ultrasonic diagnostic apparatus as recited above, that said transmitting and receiving means includes scan line intersection shift means for shifting said fourth predetermined point to said arrangement direction, and for shifting said fifth predetermined point to said arrangement direction and a depth direction within the subject.

Also in the apparatus according to the second or third type of system as recited above, similar to the apparatus according to the first type of system as recited above, it is preferable that said transmitting and receiving means performs transmitting and/or receiving of ultrasonic waves using a larger number of said piezoelectric transducers for transmitting and receiving of ultrasonic waves along the scan lines nearer a central part of the sector configuration.

Further, in the apparatus according to the first, second or third type of system as recited above, it is preferable that said transmitting and receiving means is arranged to form received signal on each scan line in such a manner that a larger weighting is applied to received signals derived from the piezoelectric transducers arranged nearer a central part of a receiving aperture comprised of a plurality of the piezoelectric transducers which serve to receive ultrasonic wave of the associated scan line, and then the signals subjected to the weighting process are added. And it is also preferable that said apparatus further comprises second transmitting and receiving means for transmitting and receiving ultrasonic waves along a plurality of scan lines which are sequentially deflected as a sector in the arrangement direction and pass through a predetermined point on said piezoelectric transducers, said second transmitting and receiving means being adapted to be replaced by said transmitting and receiving means on a switching basis.

Furthermore, in the apparatus according to the first, second or third type of system as recited above, it is preferable that said transmitting and receiving means is arranged to perform transmission of ultrasonic waves in such a manner that a higher energy of electric power is supplied to said piezoelectric transducers for transmitting of ultrasonic waves along scan lines nearer edge portions of said sector configuration. And it is preferable that said transmitting and receiving means is arranged to amplify the received signals derived through said piezoelectric transducers with a higher amplification factor for receiving of ultrasonic waves along scan lines nearer edge portions of said sector configuration.

With respect to display means, in the apparatus according to the first, second or third type of system as recited above, it is preferable that said display means displays a relative position of said piezoelectric transducers to a tomographic image of the subject, along with the tomographic image.

Further, in the apparatus according to the first, second or third type of system as recited above, in a case where there is provided the second transmitting and receiving means in addition to said transmitting and receiving means, it is acceptable that said display means displays a tomographic image of the subject based on the received signals derived through said transmitting and receiving means, and in addition a partial image of a tomographic image of the subject based on the received signals derived through said second transmitting and receiving means, said partial image being displayed on a screen area, in which the former tomographic image is not displayed, in alignment of coordinates with the former tomographic image.

Furthermore, in the apparatus according to the first, second or third type of system as recited above, it is a preferable aspect that said display means displays a tomographic image having an angle defined by two scan lines of both the edges of said sector configuration, said angle exceeding 90°. And it is acceptable that said display means displays a first tomographic image of the subject based on the received signals derived through said transmitting and receiving means, and in addition a screen area adapted to display a second tomographic image of the subject based on received signals which will be derived when ultrasonic waves are received along a plurality of scan lines which are sequentially deflected as a sector in the arrangement direction and pass through a predetermined point fixed on said piezoelectric transducers or movable on said piezoelectric transducers in the arrangement direction, said screen area being displayed in alignment of coordinates with the first tomographic image.

According to the conventional scan scheme, it is obliged to be influenced by the ribs in transmitting and receiving of ultrasonic waves, since the ribs appear on scan lines. For this reason, according to the ultrasonic diagnostic apparatus, as the first type of system, a sector center is set up within the human body (between adjacent ribs) and the sector scan is implemented with the set up position in the center. A positional relationship between the human body and the ribs is expressed such that a distance from the body surface to the ribs is of the order of 0–1 mm; a shape of a rib is almost elliptical with a dimension of the order of 12 mm in width and of the order of 8 mm in thickness; and an opening of adjacent ribs is about 10 mm. In view of such a positional relationship, if the sector center is set up to 1–6 mm in depth, preferably, 4 mm–5 mm within the human body, it is possible to perform a scan avoiding the ribs. Consequently, if transmitting and receiving of ultrasonic waves are effected through shifting a starting point of a scan line (an intersection of the scan line and the arranged piezoelectric transducers) in accordance with a deflecting angle of the scan line concerned, in such a manner that the respective scan lines intersect at a predetermined point of 1–6 mm (preferably 4 mm–5 mm) in depth within the human body, it is possible to implement a sector scan with a point (the first point) within the human body in the center.

With respect to the aperture (the number of elements) for transmitting and receiving, hitherto, the number of elements for transmitting and receiving is given by 7 to 9 elements (cf. FIGS. 29 and 30) so that the same aperture is provided for the respective scan lines. On the other hand, according to the ultrasonic diagnostic apparatus, as the first type of system of the present invention, transmitting and/or receiving of ultrasonic waves are performed using a larger number of said piezoelectric transducers for transmitting and receiving of ultrasonic waves along the scan lines nearer a central part of the sector configuration. Thus, according to the ultrasonic diagnostic apparatus, as the first type of system of the present invention, resolution and penetration are improved comparing with the conventional system. In this case, the aperture of the edge portion is smaller than that of the central part. As a result, resolution and penetration will be reduced relatively comparing with the central part. However, it is possible to avoid such a reduction by means of increasing an energy (voltage, the number of pulses and the like) for driving the piezoelectric transducers for scan lines nearer the edge portion, or increasing an amplification factor of the received signal for scan lines nearer the edge portion.

Further, moving the first predetermined point as the pivot of a sector shaped scan line to the depth direction within the subject makes it possible to control the first predetermined point to a suitable depth even if individuality (physique) of the subject is varied. Furthermore, moving the first predetermined point to the arrangement direction make it possible to observe with greater resolution one of the right and the left of the tomographic image in accordance with the moving direction.

In this manner, according to the ultrasonic diagnostic apparatus, as the first type of system of the present invention, it is possible to perform transmitting and receiving of ultrasonic waves without obstruction, thereby suppressing multiple reflection from the ribs and deterioration of images. And in addition, it is possible to improve resolution and penetration.

According to the ultrasonic diagnostic apparatus, as the second type of system of the present invention, a cross point (the second predetermined point) as to transmitting is set up shallowly more than a cross point (the third predetermined point) as to receiving. This feature permits a less moving amount of the cross point of scan lines in transmitting with the piezoelectric transducers, thereby spreading a transmitting aperture also as to the scan lines at the sector shaped edge portions. Therefore, comparing with the first type of ultrasonic diagnostic apparatus, while it is influenced somewhat by the ribs, it is possible to enhance resolution of the edge portions and intensity of the received signals by the corresponding enlargement of the transmitting aperture.

According to the ultrasonic diagnostic apparatus, as the third type of system of the present invention, with respect to transmission, in a similar fashion to that of the conventional system (cf. FIG. 27), a cross point (the fourth predetermined point) of the scan lines is set up on the piezoelectric transducers, and on the other hand, with respect to receiving only, a cross point (the fifth predetermined point) of the scan lines is set up within the subject away from the piezoelectric transducers. According to the ultrasonic diagnostic apparatus, as the third type of system of the present invention, comparing with the second type of ultrasonic diagnostic apparatus, while it is more influenced somewhat by the ribs, it is possible to enhance resolution of the edge portions and intensity of the received signals by the corresponding. Further, for example, if the above-mentioned receiving dynamic focus is used in combination, it is possible to form a tomographic image, similar to the conventional one, in which a point coming in contact with the piezoelectric transducers is provided as the pivot of the sector configuration. In this case, it is possible to perform a display which will give little a sense of disharmony for an operator who is familiar with the conventional tomographic image in observation.

Further, positioning a cross point of scan lines for transmitting and receiving within the subject away from the piezoelectric transducers makes it possible, even in a case where a sector shaped tomographic image is formed with the point located away from the piezoelectric transducers in the center, to clear a distinction from the screen of the conventional tomographic image in such a manner that a relative position of the piezoelectric transducers is displayed on the screen, the tomographic image concerned is superposed on the conventional sector shaped tomographic image formed with a point coming in contact with the piezoelectric transducers in the center, or a display image area of the conventional sector shaped tomographic image is clarified. Thus, it is possible, for an operator who is familiar with the conventional tomographic image in observation, to avoid mistake as to the corresponding between the tomographic image and the position within the subject.

Incidentally, according to the present invention, it is possible to set up the center of a sector configuration of a tomographic image inside the subject. Consequently, it is possible to display a wider-angle of tomographic image than 90° of opening angle of tomographic image according to the conventional scheme. The display of such a wide-angle of tomographic image allows observation and diagnostic over the wide area particularly as to a deep portion within the subject.

DESCRIPTION OF THE PREFERRED EMBODIMENTS

Figure 1:
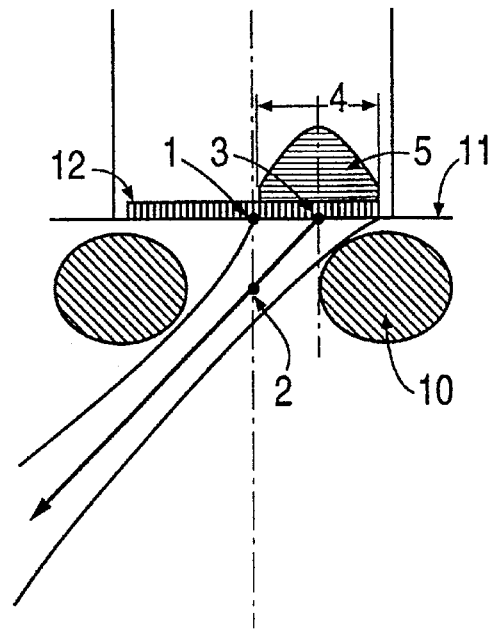
FIG. 1 is a typical illustration of ultrasonic wave transmitting and receiving according to an embodiment of the first ultrasonic diagnostic apparatus of the present invention.

Hereinafter, there will be described embodiments of the present invention.

FIGS. 1 to 4 are each a typical illustration of ultrasonic wave transmitting and receiving according to an embodiment of the first ultrasonic diagnostic apparatus of the present invention.

According to the present embodiment, it is assumed that 64 pieces of element are arranged with 0.3 mm of element pitch, and thus there is provided 19.2 mm of aperture. Transmitting and receiving are effected using a number of elements, such as the maximum 48 pieces of element for transmitting and the maximum 64 pieces of element or overall elements for receiving, as much as possible, and setting up a cross point 2 of the respective scan lines at about 5 mm of depth.

First, FIG. 1 concerns an example in which the leftmost scan line is formed.

A starting point 3 of the scan line is set up at a position shifting from the center 1 to the right side by the corresponding 17 pieces of element (about 5 mm), and the ultrasound beam is transmitted from the starting point 3 toward the left down. In this case, since 15 pieces of element remain on the right of the starting point 3, the number of elements available for transmission is 30 pieces (aperture 4) which is a maximum assuming symmetry with respect to right and left. For receiving, the same elements as transmission are used. With respect to weighting for receiving, as shown in a mountain-shaped weighting distribution 5 in the figure, the higher weighting is provided at the central part with the starting point 3 in the center, and the lower at the edge parts.

Figure 2:
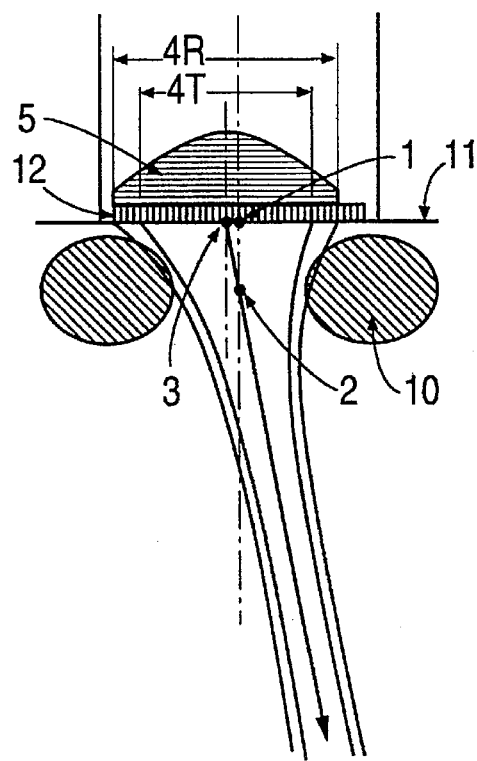
FIG. 2 is a typical illustration of ultrasonic wave transmitting and receiving according to an embodiment of the first ultrasonic diagnostic apparatus of the present invention.

Next, there will be described a case in which the scan line of the central part as shown in FIG. 2 is formed. In FIG. 2 and the following figures, suffixes "T" and "R" of reference numbers denote transmitting end and receiving end, respectively. For example, in FIG. 2, 4T and 4R denote a transmitting aperture and a receiving aperture, respectively.

The scan line shown in FIG. 2 concerns an example in which the starting point 3 is shifted to the left side by the corresponding 2 pieces of element. While the number of elements available for transmission is 60 pieces which is a maximum assuming symmetry with respect to right and left, the maximum number of elements available for transmission is set up to be 48 pieces, and thus 48 pieces of element are used for transmission. With respect to receiving, in a similar fashion to that of FIG. 1, the receiving is implemented using 60 pieces of element the number of which is a maximum assuming symmetry with respect to right and left with the starting point 3 in the center.

Figure 3:
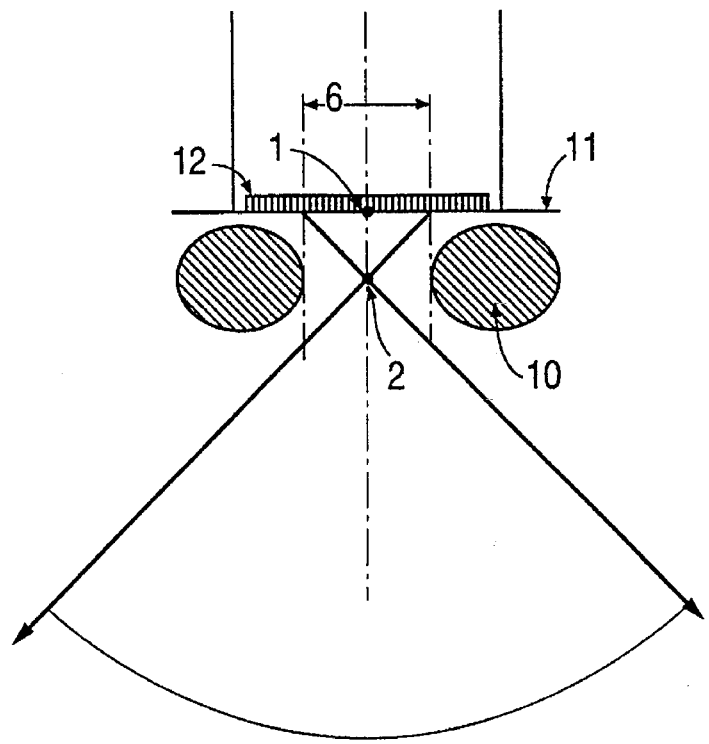
FIG. 3 is a typical illustration of ultrasonic wave transmitting and receiving according to an embodiment of the first ultrasonic diagnostic apparatus of the present invention.
Figure 5:
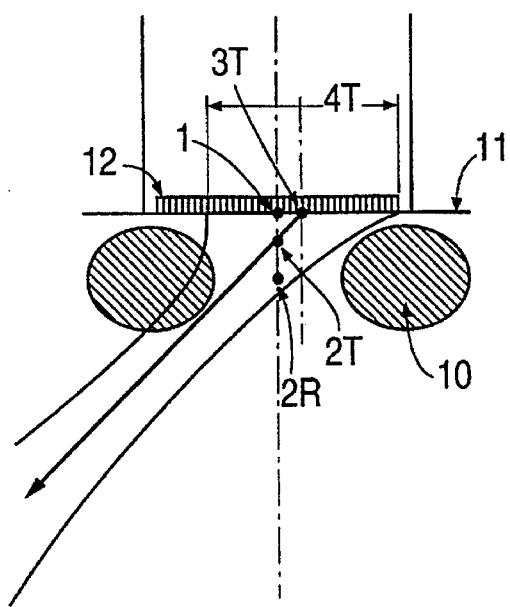
FIG. 5 is a typical illustration of ultrasonic wave transmitting and receiving according to an embodiment of the second ultrasonic diagnostic apparatus of the present invention.
Figure 4:
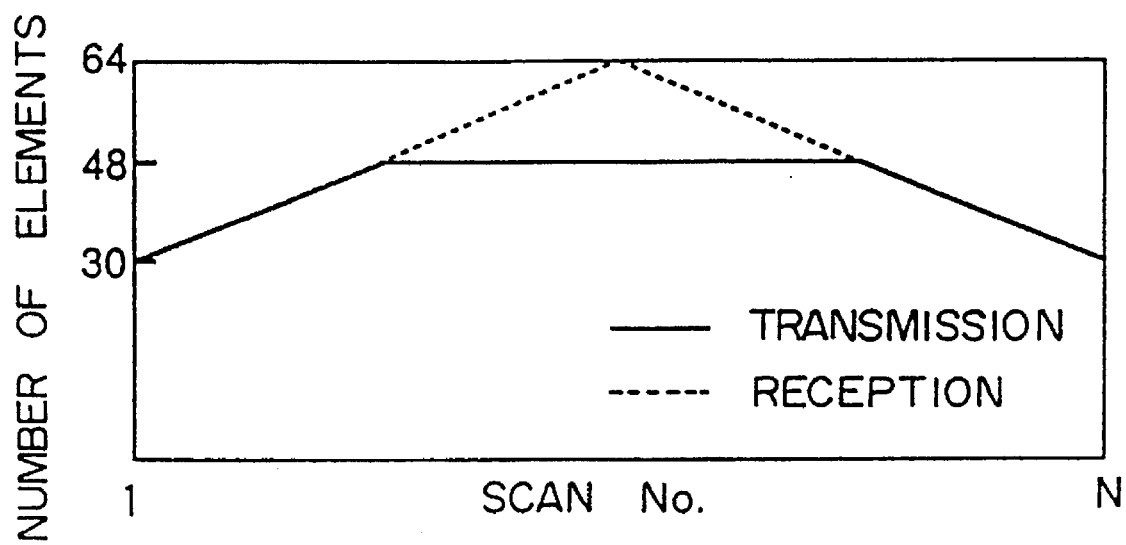
FIG. 4 is a typical illustration of ultrasonic wave transmitting and receiving according to an embodiment of the first ultrasonic diagnostic apparatus of the present invention.
Figure 6:
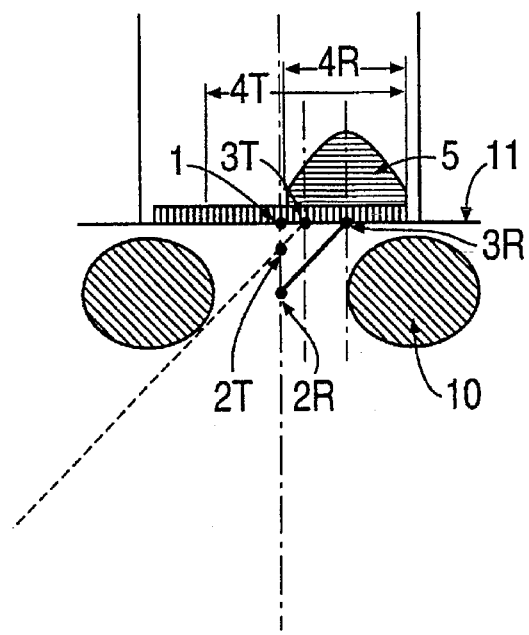
FIG. 6 is a typical illustration of ultrasonic wave transmitting and receiving according to an embodiment of the second ultrasonic diagnostic apparatus of the present invention.
Figure 7:
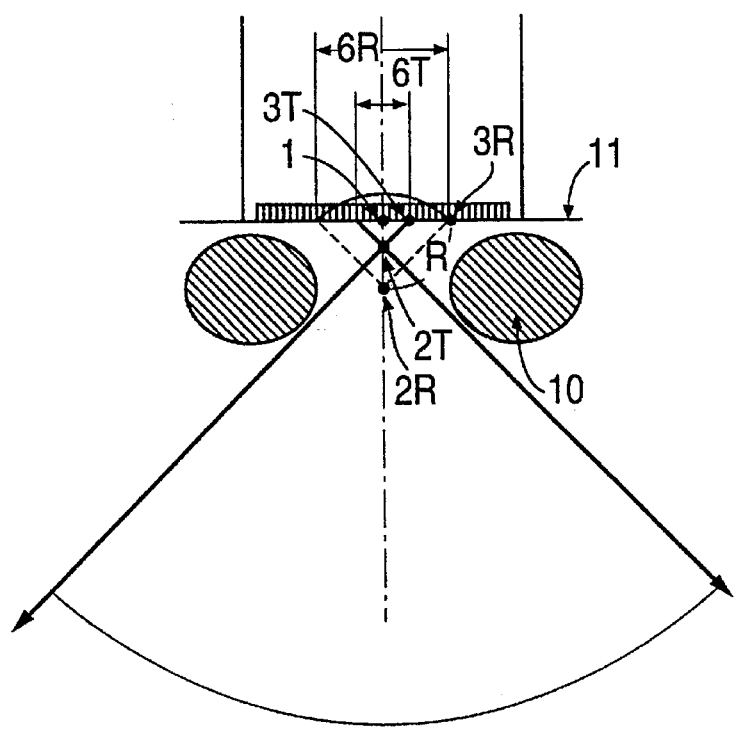
FIG. 7 is a typical illustration of ultrasonic wave transmitting and receiving according to an embodiment of the second ultrasonic diagnostic apparatus of the present invention.

Performing the transmitting and receiving scans as shown in FIGS. 1 and 2 provides, as shown in FIG. 3, a sector configuration of scan with a cross point 2 within the human body in the center. FIG. 4 shows a distribution of the number of elements for transmitting and receiving to the shift of scan lines. Incidentally, if intensity of the received signal of the scan line on the edge portion is insufficient owing to shortage of the elements, it is possible to facilitate an observation by increasing an amplification factor of the scan line on the edge portion.

Figure 8:
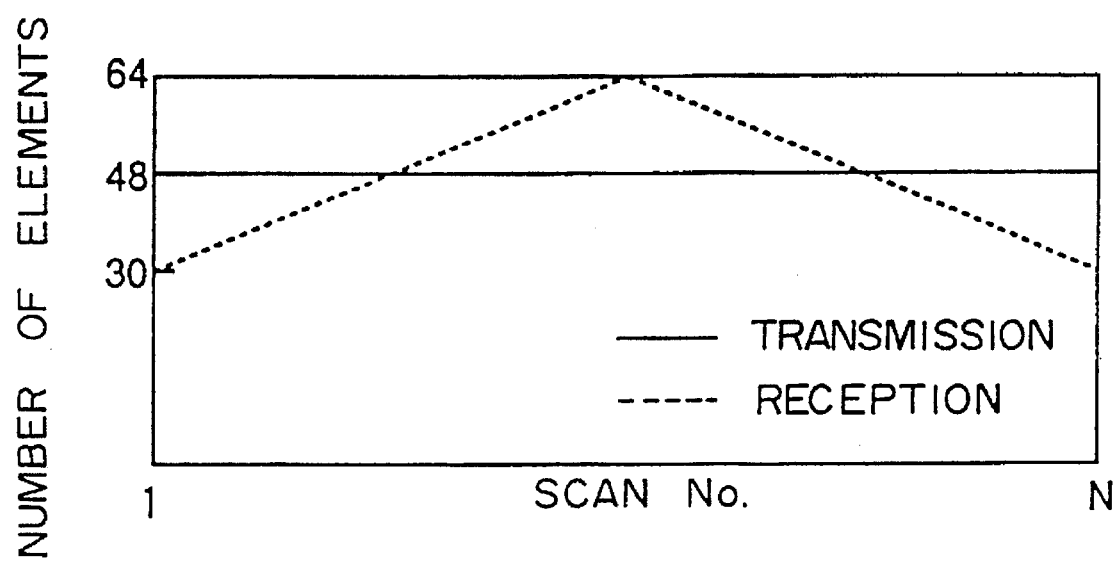
FIG. 8 is a typical illustration of ultrasonic wave transmitting and receiving according to an embodiment of the second ultrasonic diagnostic apparatus of the present invention.

FIGS. 5–8 are each a typical illustration of ultrasonic wave transmitting and receiving according to an embodiment of the second ultrasonic diagnostic apparatus of the present invention;

According to the present embodiment, as to an arrangement involved in receiving, that in the embodiment shown in FIGS. 1–4 is retained without any changes, and as to an arrangement involved in transmitting, there is so arranged that the respective scan lines on the transmitting side intersect at a position 2T of about 2.4 mm in depth which is shallower than that in the embodiment shown in FIGS. 1–4. The reason why according to the present embodiment there is so arranged that the respective scan lines on the transmitting side intersect at the position which is shallower than that in the embodiment shown in FIGS. 1–4 is that such an arrangement permits the situation that a shift amount 6T (cf. FIG. 7) of the center 3T for transmitting is less than a shift amount 6R of the center 3R for receiving. Consequently, it is sufficient for forming the edge portion scan lines to simply shift the starting point 3T from the center by the corresponding 8 elements, so that the number of elements available for transmission is 48 pieces which is a maximum assuming symmetry with respect to right and left. Thus, as shown in FIG. 8, it is possible to transmit overall scan lines using 48 elements the number of which is a maximum number of elements available for transmission. Therefore, comparing with the embodiment shown in FIGS. 2–4, while it is influenced somewhat by the ribs, it is possible to enhance resolution of the edge portions and intensity of the received signals by the corresponding enlargement of the transmitting aperture.

Figure 9:
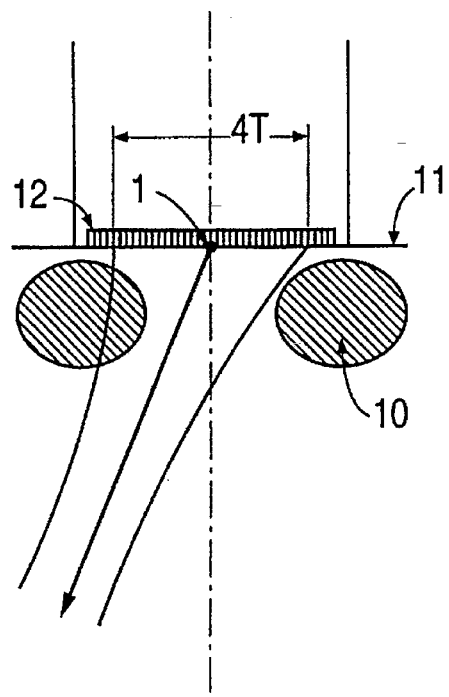
FIG. 9 is a typical illustration of ultrasonic wave transmitting and receiving according to an embodiment of the third ultrasonic diagnostic apparatus of the present invention.
Figure 10:
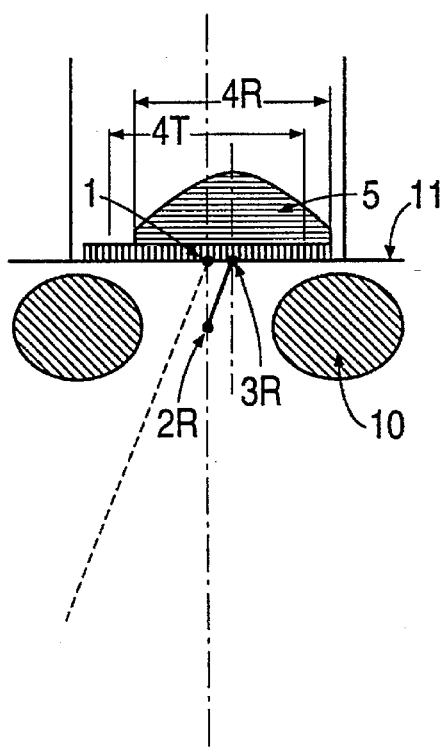
FIG. 10 is a typical illustration of ultrasonic wave transmitting and receiving according to an embodiment of the third ultrasonic diagnostic apparatus of the present invention.
Figure 11:
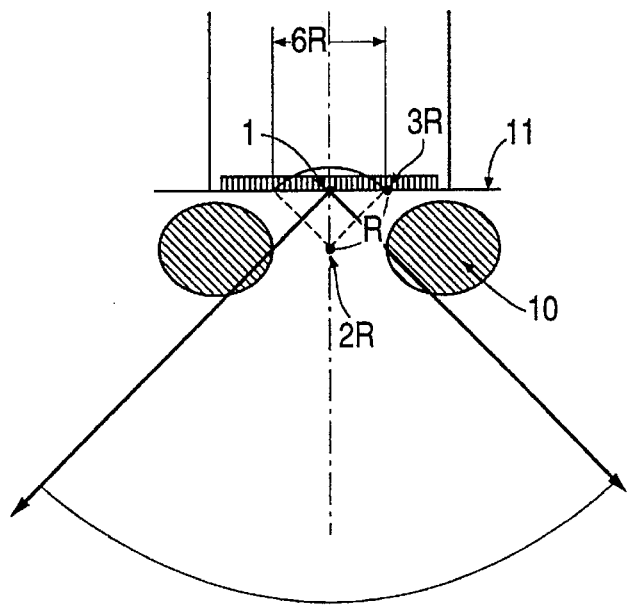
FIG. 11 is a typical illustration of ultrasonic wave transmitting and receiving according to an embodiment of the third ultrasonic diagnostic apparatus of the present invention.

FIGS. 9–11 are each a typical illustration of ultrasonic wave transmitting and receiving according to an embodiment of the third ultrasonic diagnostic apparatus of the present invention;

according to the present embodiment, as to transmitting, in a similar fashion of that of the conventional electronic sector system (cf. FIG. 27), the ultrasonic waves are transmitted with the central part 1 of the elements 12 in the center, and with respect to receiving only, this is the similar as to the matter of the embodiment shown in FIGS. 1–4 and the embodiment shown in FIGS. 5–8. As seen from FIG. 9, when the ultrasound beams are transmitted toward the left side, the left half of elements among the elements 12 receive reflecting echoes from the ribs more than that of the right half of elements. Hence, as shown in FIG. 10, only the elements of the right-hand side among the elements 12, which will receive less reflecting echoes from the ribs, are used for receiving, thereby contributing to reduction of the reflecting signals from the ribs.

Figure 12:
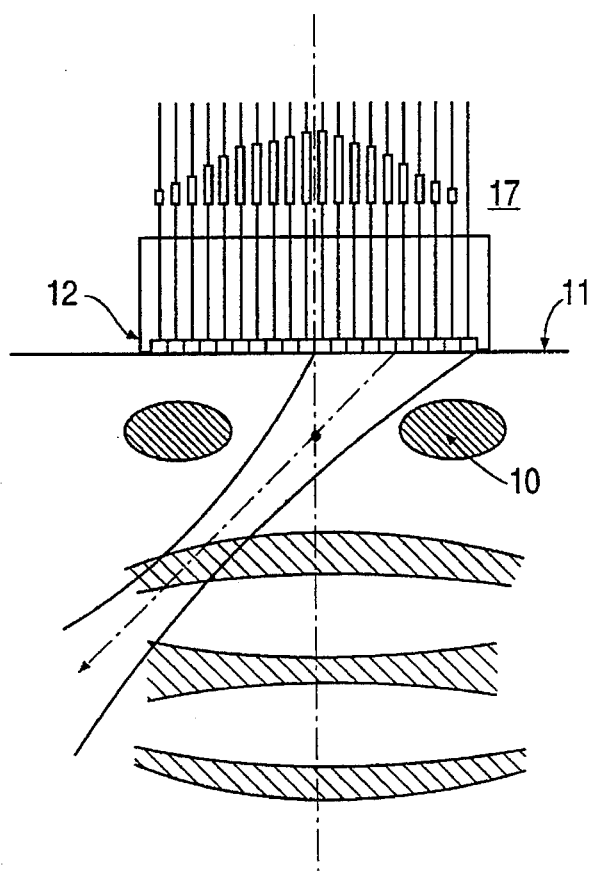
FIG. 12 is a typical illustration showing an example in which the present invention is applied to the related art.
Figure 14:
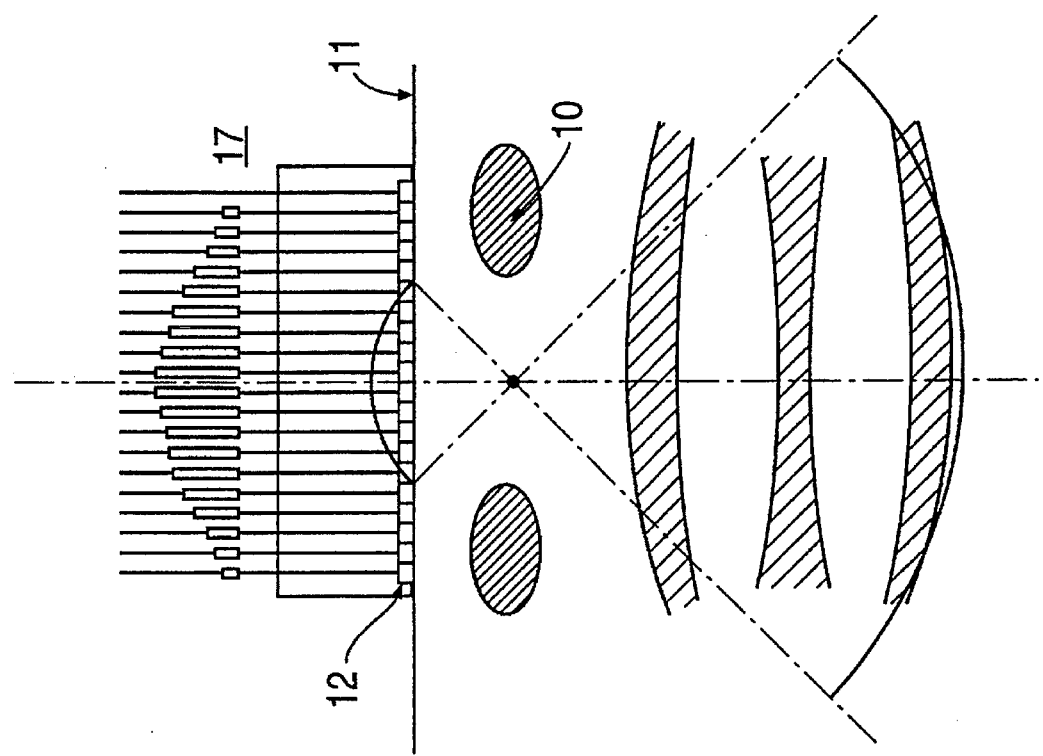
FIG. 14 is a typical illustration showing an example in which the present invention is applied to the related art.
Figure 13:
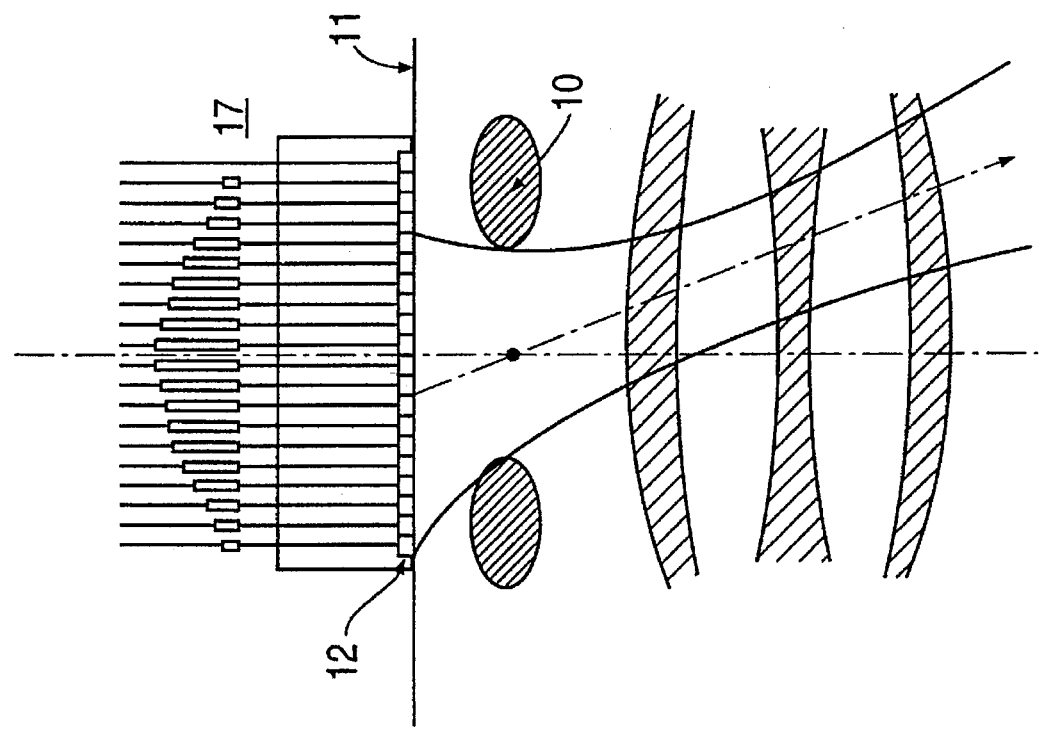
FIG. 13 is a typical illustration showing an example in which the present invention is applied to the related art.
Figure 29:
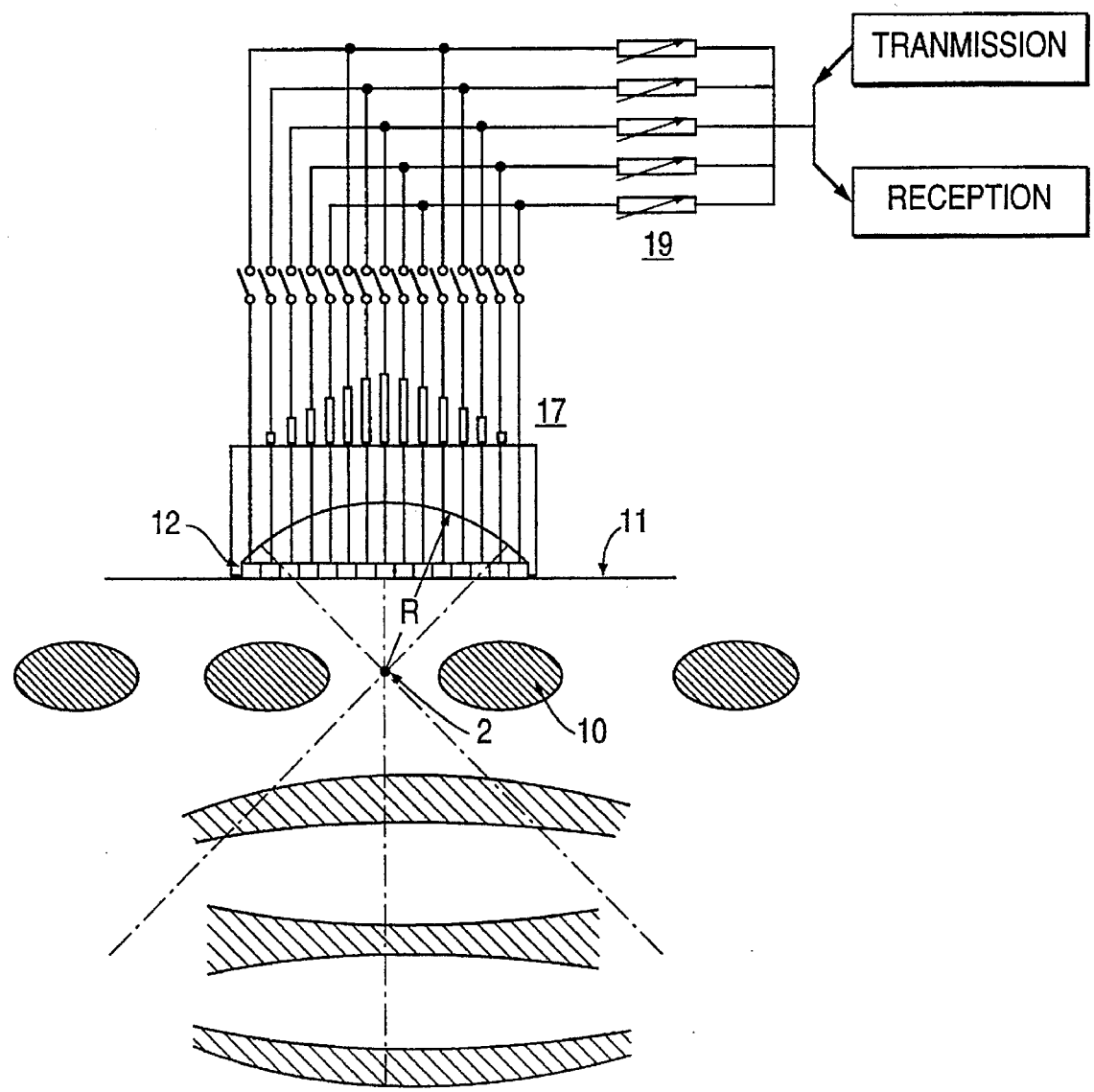
FIG. 29 is a typical illustration useful for understanding the proposal according to the related art.
Figure 30:
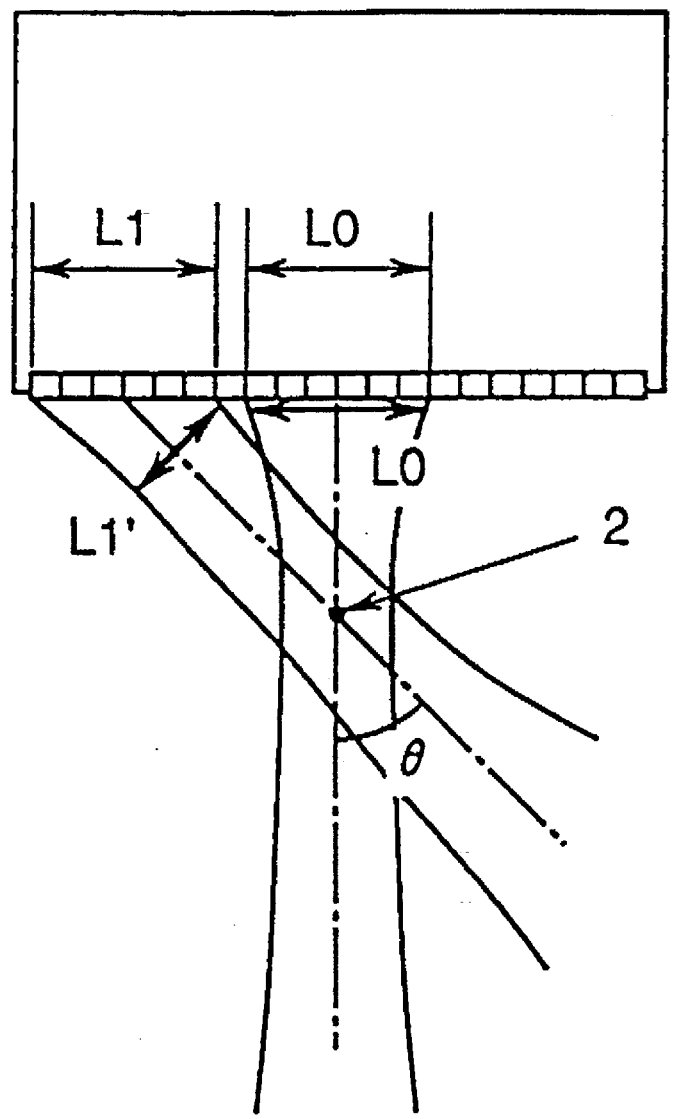
FIG. 30 is a typical illustration useful for understanding the proposal according to the related art.

FIGS. 12–14 are each a typical illustration showing an example in which the present invention is applied to the techniques (cf. FIGS. 29 and 30) proposed in Japanese Patent Publication No. 12971/1992. According to this scheme, the number of elements for transmitting and receiving is increased in comparison with the conventional scheme, thereby improving resolution and intensity of the received signals. With respect to the scan lines of the central part of the sector configuration, the number of elements for transmitting and receiving is increased in comparison with that of the edge portions, thereby improving remarkably a portion of the scanlines of the central part of the sector shaped tomographic image in the quality of image.

Figure 15:
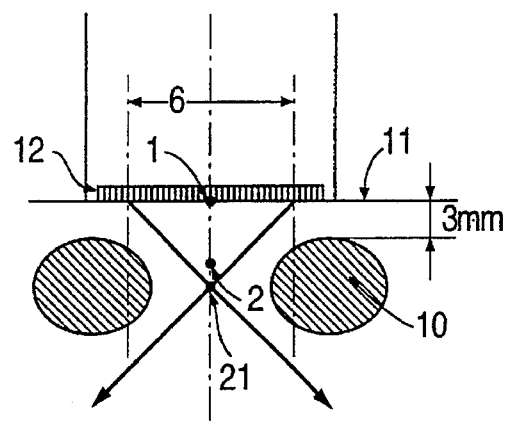
FIG. 15 is a typical illustration showing an example in which an intersection of the scan lines within the human body is varied in a scan direction and a depth direction.
Figure 16:
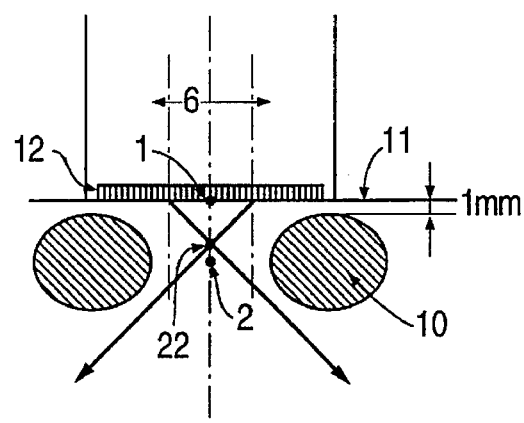
FIG. 16 is a typical illustration showing an example in which an intersection of the scan lines within the human body is varied in a scan direction and a depth direction.
Figure 17:
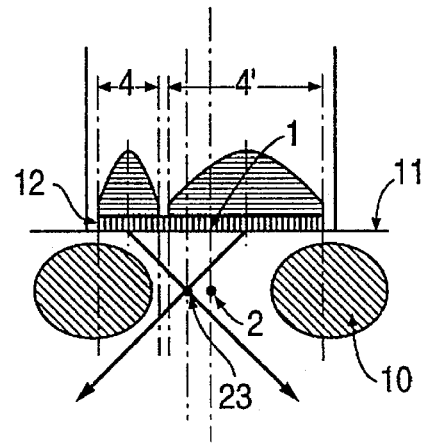
FIG. 17 is a typical illustration showing an example in which an intersection of the scan lines within the human body is varied in a scan direction and a depth direction.

FIGS. 15–17 are each a typical illustration showing an example in which an intersection of the scan lines within the human body is varied in a scan direction and a depth direction.

Since a distance from a body surface up to the ribs and an interval between adjacent ribs differ from individual to individual, it is desirable to provide, as shown in FIGS. 15 and 16, such an arrangement that a position 2 of the sector center is optionally variable in depth directions 21 and 22. Providing a variable amount of 1–6 mm in depth permits the system to be sufficiently applicable for children to adults who are on the plump side with a distance between the body surface and the ribs in the order of 8 mm. It is acceptable to mount, for example, a variable switch on a scan panel so as to control the variable amount while observing an image.

Further, if it is so arranged that the sector center 1 is optionally variable also with respect to a scan direction (right and left direction in FIGS. 15–17), then for example, in a case where a target is in the left edge portion of the screen, it is possible, as shown in FIG. 17, to shift a group of elements to the right so that the sector center can be moved to the left-hand side 23. In this manner, the number of elements for transmitting and receiving on the right-hand side is increased. An increase of the number of elements for transmitting and receiving on the right-hand side makes it possible to enhance resolution of the left-hand side portion of the image and intensity of the received signal, thereby enhancing a quality of image on the portion of the left-hand side.

Figure 27:
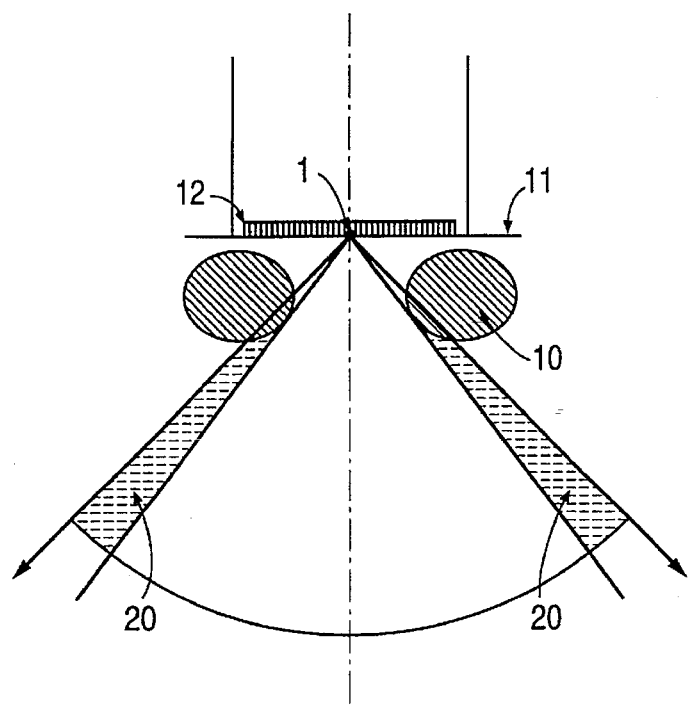
FIG. 27 is a typical illustration showing the state of transmitting and receiving of the ultrasonic waves through rib-to-rib toward the heart using the conventional electronic sector scheme of ultrasonic diagnostic apparatus.
Figure 28:
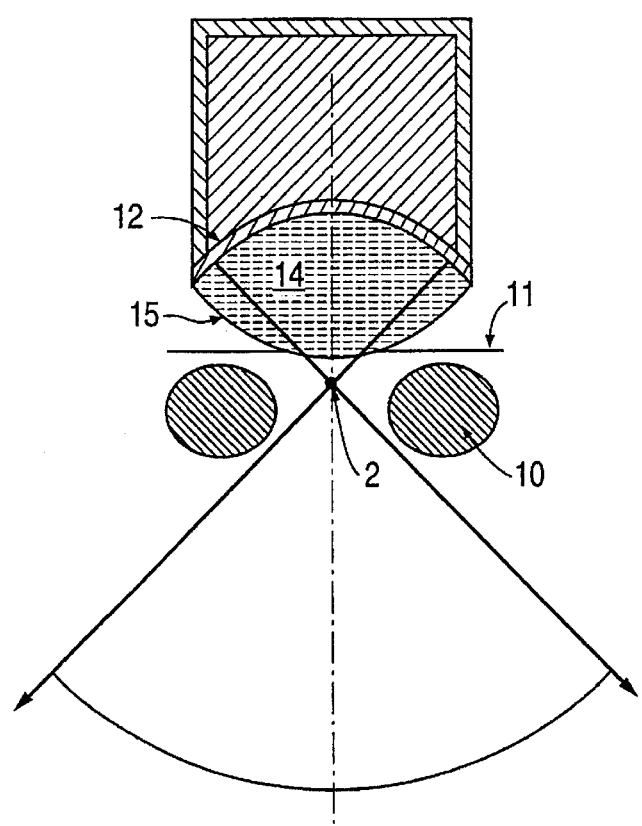
FIG. 28 is a typical illustration showing a technique of removing or reducing a bad influence of the ribs, which has been proposed in the related art.

As another embodiment, not illustrated, it is acceptable to provide on an operation panel a switch for change-over of a sector mode so as to be switched also to the conventional sector scan (cf. FIG. 27). Providing an additional function of change-over of a sector mode permits the system of the invention to be used for a case other than the case of diagnostic of the heart through an opening between adjacent ribs.

Incidentally, according to the system of the present invention, the number of elements for transmitting is reduced with nearer scan lines to the edge portions larger in an amount of shift of the center 2 of a group of elements for transmitting and receiving. This will invite a lower transmitting sound pressure on the edge portion. Further, since the number of elements for receiving is also reduced, intensity of the received signal is reduced. This will invite darkness on the edge portions when displayed in the form of image, and thus be in danger of assuming image hard to see. For these reasons, according to the present invention, there is provided an additional function in which a drive voltage increases with nearer scan lines to the edge portions to enhance the transmitting sound pressure, thereby improving an S/N ratio. Further, if there is provided a function in which an amplification factor is enhanced with nearer scan lines to the edge portions, it is possible to prevent the edge portions from being displayed with dark images, thereby assuming images easy to see.

Next, there will be described an example involved in an image display.

Figure 18:
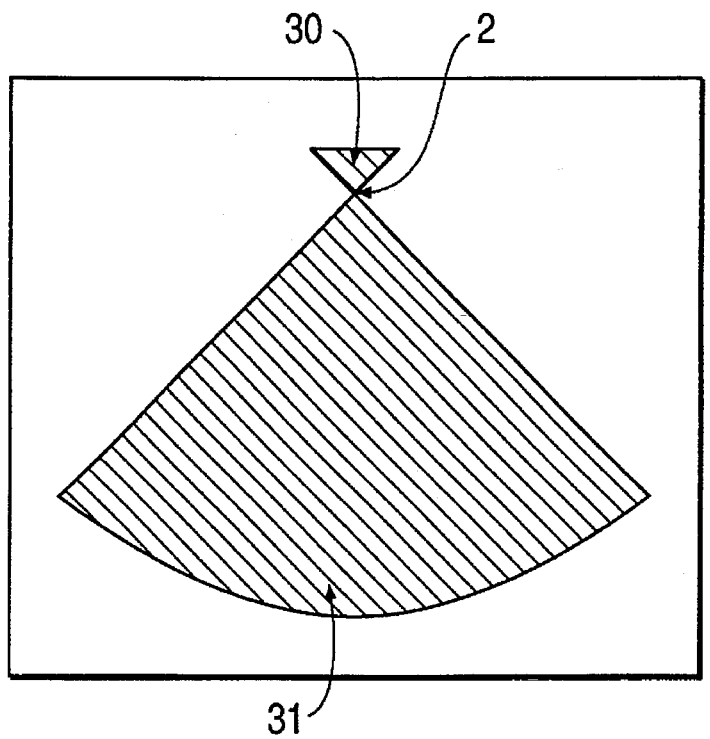
FIG. 18 is an illustration showing the first example in which information as to the depth direction is displayed.

FIG. 18 is an illustration showing the first example in which information as to the depth direction is displayed.

When the sector center according to the present invention is set up within the human body (between adjacent ribs) and is varied optionally, if a tomographic image 31 of only a portion deeper than the sector center is displayed in a similar fashion to that of the conventional sector scan, there is the possibility that the position of the depth direction can not be grasped. For this reason, there is displayed also a tomographic image 30 from a surface of the elements to the sector center, thereby facilitating understanding a relative position relation of the elements and the tomographic image. As another method, instead of no display of the tomographic image 30 shown in FIG. 18, it is acceptable to display information as to a distance from the surface of the elements on a scale basis, or to display a position of the surface of the elements. Further, as shown in FIG. 19, if there are displayed coordinates provided by a sector display from the center 1 of the elements along with a tomographic image 31 according to the present invention, it will be easy to use for an operator who is used to the conventional display scheme for the tomographic image and an operator who uses the sector scan according to the present invention and the sector scan according to the conventional scheme on a switching basis, since there is no remarkable changes on the screen.

Figure 20:
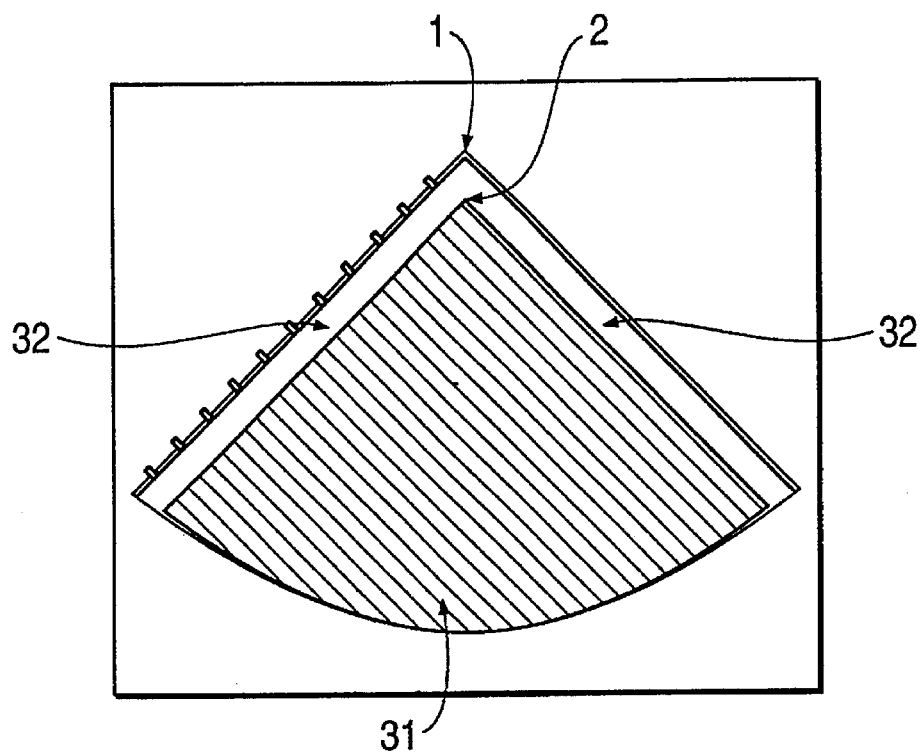
FIG. 20 is an illustration showing an example in which an image interpolation is effected.
Figure 21:
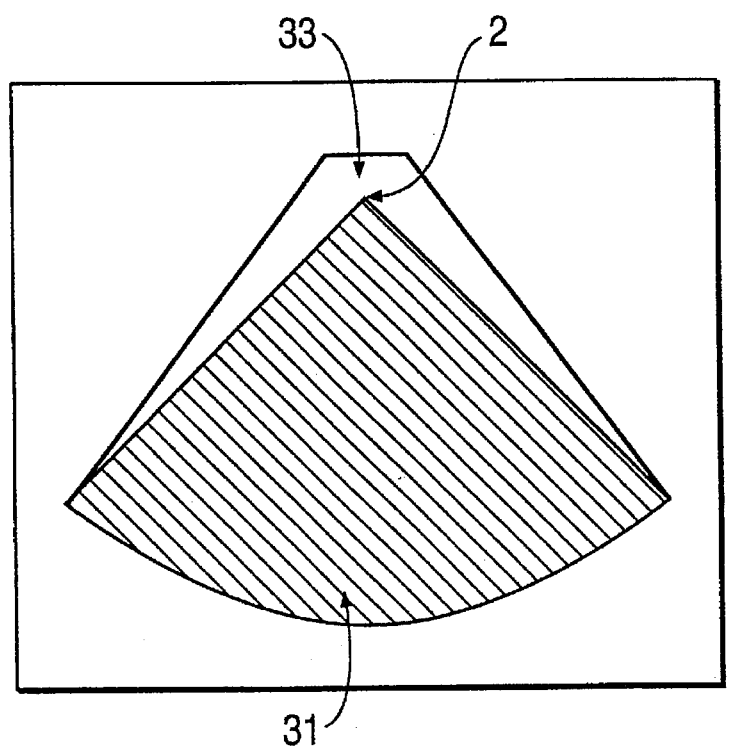
FIG. 21 is an illustration showing an example in which an image interpolation is effected.

FIGS. 20 and 21 are each an illustration showing an example in which an image interpolation is effected.

Figure 19:
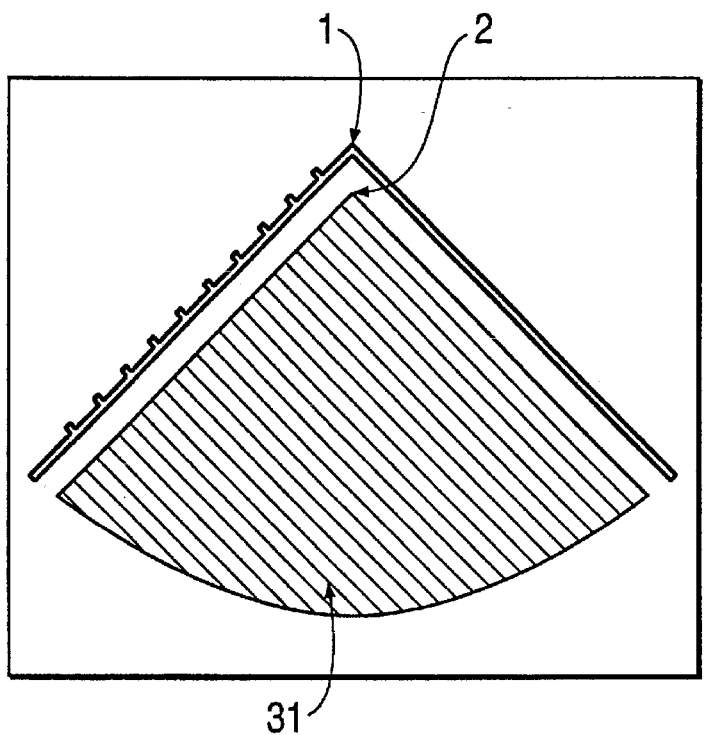
FIG. 19 is an illustration showing an example in which coordinates of a tomographic image according to the conventional sector scan is displayed along with a tomographic image according to the present invention.

FIG. 20 illustrates an example in which an image interpolation is effected in a remaining area 32 other than a display area of the tomographic image 31 according to the present invention, in the conventional sector scan in FIG. 19. As an example of an image to be interpolated, there are considered a tomographic image formed through the conventional sector scan taking with the sector center 1 in the center of the sector configuration, or a uniform brightness of image and the like. Further, according to an example shown in FIG. 21, as an interpolating image, there is used an image in a case where a trapezoid scan is effected with a shift width 6 (cf. FIG. 3) of the starting point 3 (cf. FIG. 1) of the scan lines as an aperture.

Figure 22:
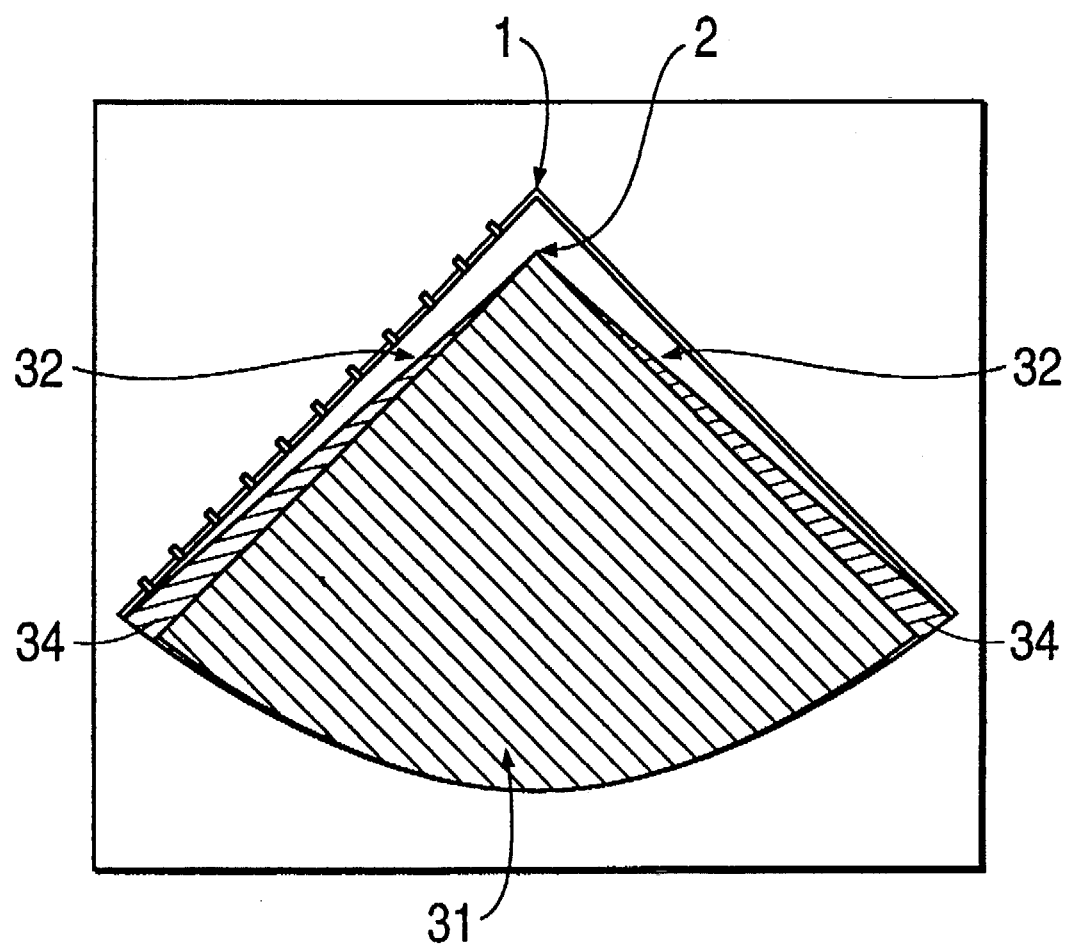
FIG. 22 is an illustration showing an example as to an image display according to the present invention.
Figure 23:
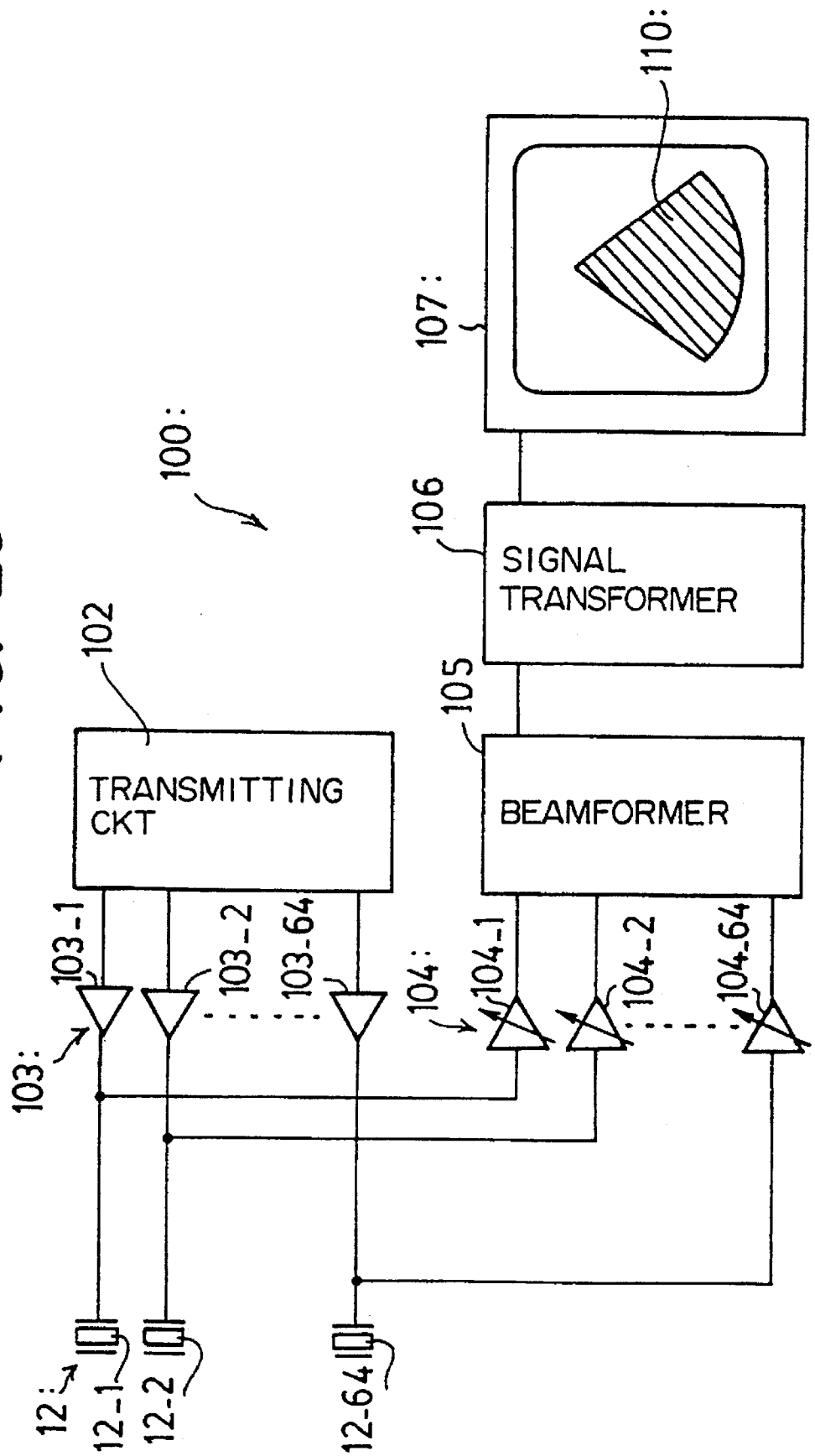
FIG. 23 is a schematic diagram showing a functional structure of an ultrasonic diagnostic apparatus.
Figure 24:
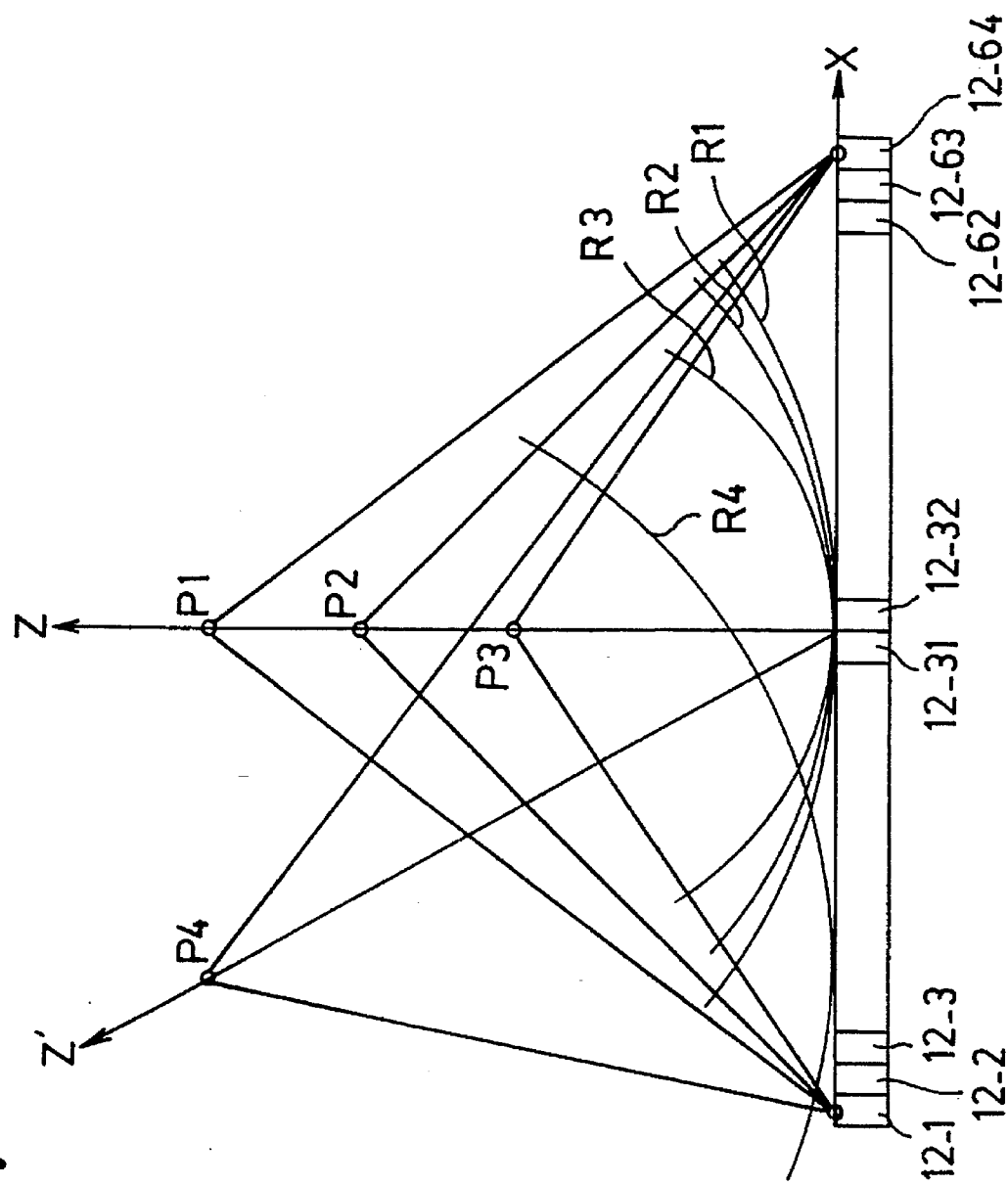
FIG. 24 is a typical illustration of an example showing a relationship between an arrangement of the piezoelectric transducers and reflecting points of ultrasonic waves within the subject.
Figure 25:
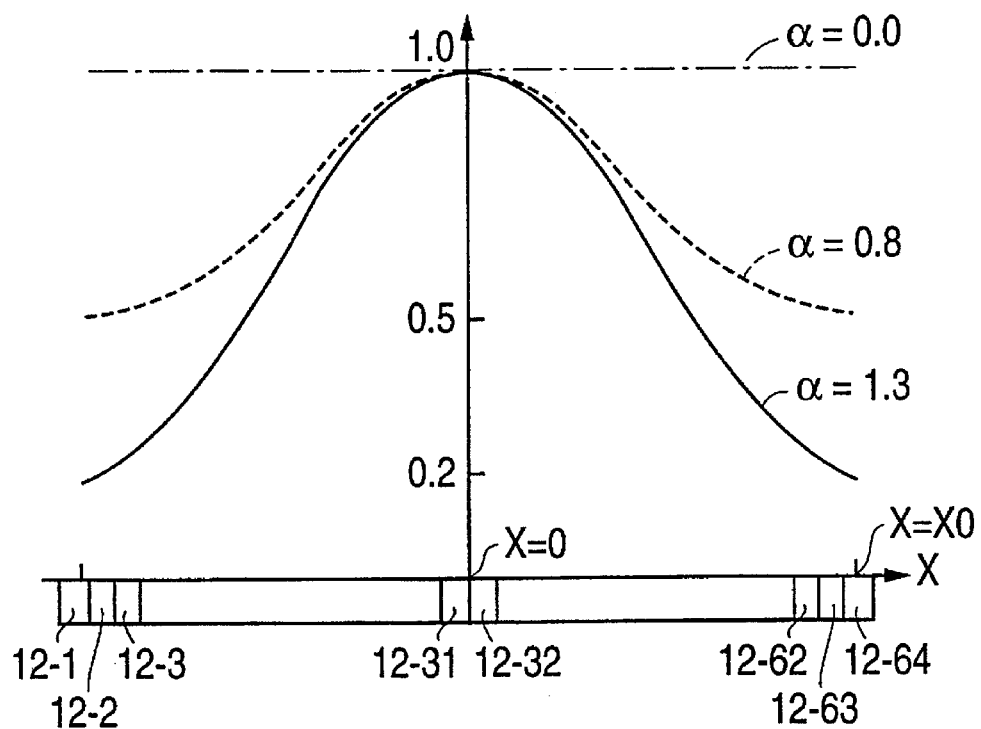
FIG. 25 is an illustration showing a pattern of weighting for the respective received signals derived through the elements.
Figure 26:
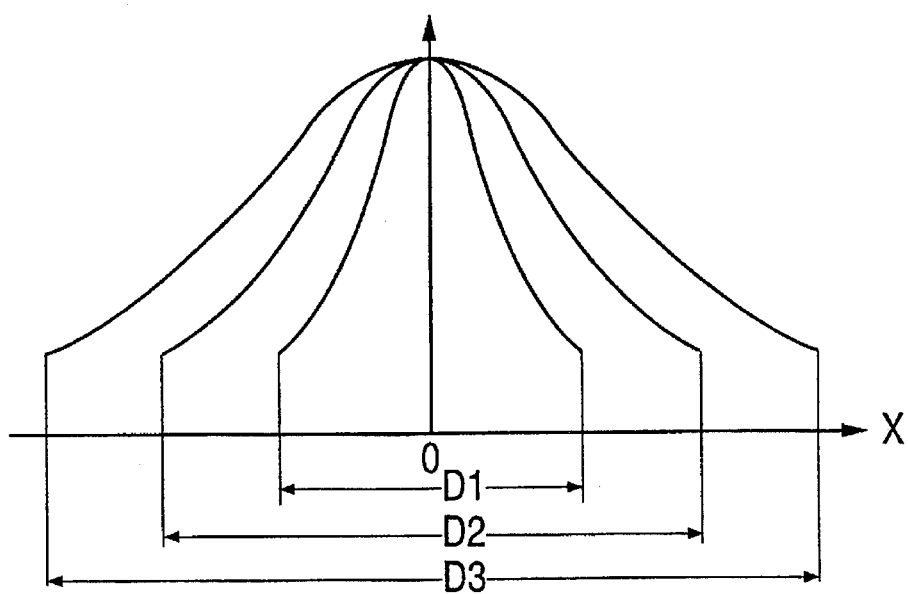
FIG. 26 is an illustration showing an example in which a size of the receiving aperture is varied in a state that weighting is fixed.

FIG. 22 is an illustration showing the fourth example as to an image display according to the present invention.

According to the present invention, the ultrasonic waves are transmitted and received avoiding the ribs, and thus the field of the vision is narrowed by the corresponding area 32 portion in comparison with the conventional sector scan. For this reason, according to the present embodiment, a scan angle is spread exceeding 90°, so that a deep portion can be seen over the wide range. According to the conventional scan scheme in which a scan is performed in a sector configuration from the center 1 of the elements, even if the scan angle is spread, the ultrasonic waves will be obstructed by the ribs. And thus, it is difficult to expect the effect. On the contrary, the scan scheme according to the present invention makes it possible to see the deep portion over the wide range.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. An ultrasonic diagnostic apparatus comprising:

transmitting and receiving means, having a plurality of piezoelectric transducers arranged in a predetermined arrangement direction, for sequentially transmitting ultrasound beams into a subject along a plurality of scan lines from the piezoelectric transducers and for sequentially receiving ultrasonic waves along a plurality of scan lines with the piezoelectric transducers; and display means for displaying a tomographic image of the subject on the basis of signals generated by said transmitting and receiving means and received by the display means, wherein said transmitting and receiving means is arranged to transmit and receive ultrasonic waves along a plurality of scan lines which are sequentially deflected as a sector in the arrangement direction and pass through a predetermined point within the subject apart from said piezoelectric transducers, and arranged such that when transmitting and receiving ultrasonic waves along scan lines near a central part of the sector, a larger number of said piezoelectric transducers are used than are used when transmitting and receiving ultrasonic waves along the scan lines near edge portions of the sector.

2. An apparatus according to claim 1, wherein a distance $d_1$ between said piezoelectric transducers and said predetermined point is expressed by $1 \text{ mm} \leq d_1 \leq 6 \text{ mm}$.

3. An apparatus according to claim 1, wherein said transmitting and receiving means includes scan line intersection shift means for shifting said predetermined point along said arrangement direction and along a depth direction within the subject.

4. An apparatus according to claim 1, wherein said transmitting and receiving means is arranged to form received signal on each scan line in such a manner that a larger weighting is applied to received signals derived from the piezoelectric transducers arranged nearer a central part of a receiving aperture comprised of a plurality of the piezoelectric transducers which serve to receive ultrasonic wave of the associated scan line, and then the signals subjected to the weighting process are added.

5. An apparatus according to claim 1, wherein said apparatus further comprises second transmitting and receiving means for transmitting and receiving ultrasonic waves along a plurality of scan lines which are sequentially deflected as a sector in the arrangement direction and after deflection, pass through a predetermined point on said piezoelectric transducers, said second transmitting and receiving means being adapted to be replaced by said transmitting and receiving means on a switching basis.

6. An apparatus according to claim 5, wherein said display means displays a tomographic image of the subject based on the signals generated by said transmitting and receiving means, and displays a partial tomographic image of the subject based on signals generated by said second transmitting and receiving means, said partial image being displayed on a screen area, in which the tomographic image is not displayed, the partial tomographic image having the same alignment coordinates as the tomographic image.

7. An apparatus according to claim 1, wherein said transmitting and receiving means is arranged to perform transmission of ultrasonic waves in such a manner that a higher energy of electric power is supplied to the piezoelectric transducers which transmit ultrasonic waves travelling along scan lines near edge portions of said sector when transmitting ultrasonic waves along scan lines near edge potions of said sector.

8. An apparatus according to claim 1, wherein said transmitting and receiving means is arranged to amplify the signals derived from ultrasonic waves received by said piezoelectric transducers, a higher amplification factor being used for received ultrasonic waves travelling along scan lines near edge portions of said sector.

9. An apparatus according to claim 1, wherein said transmitting and receiving means is arranged to amplify the signals derived from ultrasonic waves received by said piezoelectric transducers, a higher amplification factor being used for received ultrasonic waves travelling along scan lines near edge portions of said sector.

10. An apparatus according to claim 1, wherein said display means simultaneously displays the tomographic image and the relative position of said piezoelectric transducers with respect to the tomographic image.

11. An apparatus according to claim 1, wherein the tomographic image displayed by the display means has an angle defined by the edges of said sector, said angle exceeding 90°.

12. An apparatus according to claim 1, wherein said display means displays as a first image, the tomographic image of the subject based on the signals generated by said transmitting and receiving means, and displays as a second image, a tomographic image of the subject based on signals derived from ultrasonic waves received along a plurality of scan lines which are sequentially deflected as a sector in the arrangement direction and after deflection, pass through a predetermined point on said piezoelectric transducers, said second image having display coordinates aligned with display coordinates of the first image.

13. An ultrasonic diagnostic apparatus comprising:

transmitting and receiving means, having a plurality of piezoelectric transducers arranged in a predetermined arrangement direction, for sequentially transmitting ultrasound beams along a plurality of scan lines from the piezoelectric transducers into a subject and for sequentially receiving ultrasonic waves along a plurality of scan lines with the piezoelectric transducers; and display means for displaying a tomographic image of the subject on the basis of signals generated by said transmitting and receiving means and received by the display means, wherein said transmitting and receiving means are arranged to transmit ultrasonic waves along a plurality of scan lines which are sequentially deflected as a sector in the arrangement direction and before deflection, pass through a first predetermined point within the subject apart from said piezoelectric transducers; are arranged such that when transmitting and receiving ultrasonic waves along scan lines near a central part of the sector, a larger number of said piezoelectric transducers are used than are used when transmitting and receiving ultrasonic waves along the scan lines near edge portions of the sector; and are arranged to receive ultrasonic waves along a plurality of scan lines which are sequentially deflected as a sector in the arrangement direction and after deflection, pass through a second predetermined point within the subject, the second predetermined point being set deeper within the subject and further from the piezoelectric transducers than the first predetermined point.

14. An apparatus according to claim 13, wherein a distance $d_2$ between said piezoelectric transducers and said first predetermined point is expressed by 1 mm $\leq d_2 \leq$ 3 mm, and a distance $d_3$ between said piezoelectric transducers and said second predetermined point is expressed by $d_2 < d_3 \leq$ 6 mm.

15. An apparatus according to claim 13, wherein said transmitting and receiving means includes scan line intersection shift means for shifting said first predetermined point and said second predetermined point along said arrangement direction and along a depth direction within the subject.

16. An apparatus according to claim 13, wherein said transmitting and receiving means is arranged such that when transmitting and receiving ultrasonic waves along scan lines near a central part of the sector, a larger number of said piezoelectric transducers are used than are used when transmitting and receiving ultrasonic waves along the scan lines near edge portions of the sector.

17. An apparatus according to claim 13, wherein said transmitting and receiving means is arranged such that when transmitting and receiving ultrasonic waves along scan lines near a central part of the sector, a larger number of said piezoelectric transducers are used than are used when transmitting and receiving ultrasonic waves along the scan lines near edge portions of the sector.

18. An apparatus according to claim 13, wherein said transmitting and receiving means is arranged to form received signal on each scan line in such a manner that a larger weighting is applied to received signals derived from the piezoelectric transducers arranged nearer a central part of a receiving aperture comprised of a plurality of the piezoelectric transducers which serve to receive ultrasonic wave of the associated scan line, and then the signals subjected to the weighting process are added.

19. An apparatus according to claim 13, wherein said apparatus further comprises second transmitting and receiving means for transmitting and receiving ultrasonic waves along a plurality of scan lines which are sequentially deflected as a sector in the arrangement direction and after deflection, pass through a predetermined point on said piezoelectric transducers, said second transmitting and receiving means being adapted to be replaced by said transmitting and receiving means on a switching basis.

20. An apparatus according to claim 19, wherein said display means displays a tomographic image of the subject based on the signals generated by said transmitting and receiving means, and displays a partial tomographic image of the subject based on signals generated by said second transmitting and receiving means, said partial image being displayed on a screen area, in which the tomographic image is not displayed, the partial tomographic image having the same alignment coordinates as the tomographic image.

21. An apparatus according to claim 13, wherein said transmitting and receiving means is arranged to perform transmission of ultrasonic waves in such a manner that a higher energy of electric power is supplied to the piezoelectric transducers which transmit ultrasonic waves travelling along scan lines near edge portions of said sector when transmitting ultrasonic waves along scan lines near edge portions of said sector.

22. An apparatus according to claim 13, wherein said display means simultaneously displays the tomographic image and the relative position of said piezoelectric transducers with respect to the tomographic image.

23. An apparatus according to claim 13, wherein the tomographic image displayed by the display means has an angle defined by the edges of said sector, said angle exceeding 90°.

24. An apparatus according to claim 13, wherein said display means displays as a first image, the tomographic image of the subject based on the signals generated by said transmitting and receiving means, and displays as a second image, a tomographic image of the subject based on signals derived from ultrasonic waves received along a plurality of scan lines which are sequentially deflected as a sector in the arrangement direction and after deflection, pass through a predetermined point on said piezoelectric transducers, said second image having display coordinates aligned with display coordinates of the first image.

25. An ultrasonic diagnostic apparatus comprising:

transmitting and receiving means, having a plurality of piezoelectric transducers arranged in a predetermined arrangement direction, for sequentially transmitting ultrasound beams along a plurality of scan lines from the piezoelectric transducers into a subject and for sequentially receiving ultrasonic waves along a plurality of scan lines with the piezoelectric transducers; and display means for displaying a tomographic image of the subject on the basis of signals generated by said transmitting and receiving means and received by the display means, wherein said transmitting and receiving means are arranged to transmit ultrasonic waves along a plurality of scan lines which are sequentially deflected as a sector in the arrangement direction and before deflection, pass through a first predetermined point on said piezoelectric transducers; are arranged such that when transmitting and receiving ultrasonic waves along scan lines near a central part of the sector, a larger number of said piezoelectric transducers are used than are used when transmitting and receiving ultrasonic waves along the scan lines near edge portions of the sector;, and are arranged to receive ultrasonic waves along a plurality of scan lines which are sequentially deflected as a sector in the arrangement direction and after deflection, pass through a second predetermined point within the subject apart from said piezoelectric transducers.

26. An apparatus according to claim 25, wherein a distance $d_5$ between said piezoelectric transducers and said second predetermined point is expressed by 1 mm $\leq d_5 \leq$ 6 mm.

27. An apparatus according to claim 25, wherein said transmitting and receiving means includes scan line intersection shift means for shifting said first predetermined point along said arrangement direction, and for shifting said second predetermined point along said arrangement direction and along a depth direction within the subject.

28. An apparatus according to claim 25, wherein said transmitting and receiving means is arranged to form received signal on each scan line in such a manner that a larger weighting is applied to received signals derived from the piezoelectric transducers arranged nearer a central part of a receiving aperture comprised of a plurality of the piezoelectric transducers which serve to receive ultrasonic wave of the associated scan line, and then the signals subjected to the weighting process are added.

29. An apparatus according to claim 25, wherein said apparatus further comprises second transmitting and receiving means for transmitting and receiving ultrasonic waves along a plurality of scan lines which are sequentially deflected as a sector in the arrangement direction and after deflection, pass through a predetermined point on said piezoelectric transducers, said second transmitting and receiving means being adapted to be replaced by said transmitting and receiving means on a switching basis.

30. An apparatus according to claim 29, wherein said display means displays a tomographic image of the subject based on the signals generated by said transmitting and receiving means, and displays a partial tomographic image of the subject based on signals generated by said second transmitting and receiving means, said partial image being displayed on a screen area, in which the tomographic image is not displayed, the partial tomographic image having the same alignment coordinates as the tomographic image.

31. An apparatus according to claim 25, wherein said transmitting and receiving means is arranged to perform transmission of ultrasonic waves in such a manner that a higher energy of electric power is supplied to the piezoelectric transducers which transmit ultrasonic waves travelling along scan lines near edge portions of said sector when transmitting ultrasonic waves along scan lines near edge portions of said sector.

32. An apparatus according to claim 25, wherein said transmitting and receiving means is arranged to amplify the signals derived from said ultrasonic waves received by said piezoelectric transducers, a higher amplification factor being used for received receive ultrasonic waves travelling along scan lines near edge portions of said sector.

33. An apparatus according to claim 25, wherein said display means simultaneously displays the tomographic image and the relative position of said piezoelectric transducers with respect to the tomographic image.

34. An apparatus according to claim 25, wherein the tomographic image displayed by the display means has an angle defined by the edges of said sector, said angle exceeding 90°.

35. An apparatus according to claim 25, wherein said display means displays as a first image, the tomographic image of the subject based on the signals generated by said transmitting and receiving means, and displays as a second image, a tomographic image of the subject based on signals derived from ultrasonic waves received along a plurality of scan lines which are sequentially deflected as a sector in the arrangement direction and after deflection, pass through a predetermined point on said piezoelectric transducers, said second image having display coordinates aligned with display coordinates of the first image.

* * * * *